US008603797B2

(12) United States Patent
March et al.

(10) Patent No.: US 8,603,797 B2
(45) Date of Patent: Dec. 10, 2013

(54) METHODS AND COMPOSITIONS FOR TARGETED MUTAGENESIS IN BACTERIA

(75) Inventors: John C. March, Ithaca, NY (US); Matthew S. Russell, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/634,995

(22) PCT Filed: Mar. 17, 2011

(86) PCT No.: PCT/US2011/028804
§ 371 (c)(1),
(2), (4) Date: Sep. 14, 2012

(87) PCT Pub. No.: WO2011/116184
PCT Pub. Date: Sep. 22, 2011

(65) Prior Publication Data
US 2013/0023053 A1    Jan. 24, 2013

Related U.S. Application Data

(60) Provisional application No. 61/314,828, filed on Mar. 17, 2010.

(51) Int. Cl.
*C12N 1/12* (2006.01)
*C12N 1/20* (2006.01)

(52) U.S. Cl.
USPC .................................. 435/252.1; 435/252.3

(58) Field of Classification Search
None
See application file for complete search history.

(56) References Cited

U.S. PATENT DOCUMENTS

2009/0311790 A1    12/2009  Ogawa et al.

FOREIGN PATENT DOCUMENTS

WO    03/102213 A2    12/2003

OTHER PUBLICATIONS

Ang et al., Abstracts of Papers of the American Chemical Society 229, U223-U223 (2005a).
Ang, E.L. et al., "Recent advances in the bioremediation of persistent organic pollutants via biomolecular engineering" Enzyme and Microbial Technology (2005) pp. 487-496, vol. 37, No. 5.
Burnouf, D.Y. et al., "Structural and Biochemical Analysis of Sliding Clamp/Ligand Interactions Suggest a Competition Between Replicative and Transiesion DNA Polymerases" Journal of Molecular Biology (2004) pp. 1187-1197, vol. 335, No. 5.
Camps, M. et al., "Targeted Gene Evolution in *Escherichia coli* Using a Highly Error-Prone DNA Polymerase I" Proc Nati Acad Sci USA (Aug. 19, 2003) pp. 9727-9732, vol. 100, No. 17.
Cherepanov, P.P. et al., "Gene disruption in *Escherichia coli*: To R and Km R cassettes with the option of Flp-catalyzed excision of the antibiotic-resistance determinant" Gene (1995) pp. 9-14, vol. 158, No. 1.
Choi, K.H. et al.,"Mini-Tn7 Insertion in Bacteria With Single attTn7 Sites: Example *Pseudomonas aeruginosa*" Nat Protoc (2006) pp. 153-161, vol. 1, No. 1.
Chung, C.T. et al., "one-step preparation of competent *Escherichia coli*: Transformation and storage of bacterial cells in the same solution" Proc Natl Aced Sci USA(Apr. 1989) pp. 2172-2175, vol. 86.
Cupples, C.G. et al., "A set of lacZ mutations in *Escherichia coli* that allow rapid detaction of each of the six base substitutions" Proc Natl Acad Sci USA (Jul. 1989) pp. 5345-5349, vol. 86, No. 14.
Datsenko, K.A. et al., "One-step inactivation of chromosomal genes in *Escherichia coil* K-12 using PCR products" Proc Natl Acad Sci USA (Jun. 6, 2000) pp. 6640-6645, vol. 97, No. 12.
Diaz, E. et al., "Biodegradation of Aromatic Compounds by *Escherichia coli*" Microbiology and Molecular Biology Reviews (Dec. 2001) pp. 523-569, vol. 65, No. 4.
Foster, P.L., "Methods for Determining Spontaneous Mutation Rates" Methods Enzymol (2006) pp. 195-213, vol. 409.
Fuchs, R.P. et al., "Properties and Functions of *Escherichia coli*: Pol IV and Pol V" Advances in Protein Chemistry (2004) pp. 229-264, vol. 69.
Fujii, S. et al., "The Biochemical Requirements of DNA Polymerase V-mediated Translesion Synthesis Revisited" Journal of Molecular Biology (2004) pp. 405-417, vol. 341, No. 2.
Furukawa, K., "Oxygenases and Dehalogenases: Molecular Approaches to Efficient Degradation of Chlorinated Environmental Pollutants" Bioscience Biotechnology and Biochemistry (2006) pp. 2335-2348, vol. 70, No. 10.
Jones, M. E., "Accounting for Plating Efficiency When Estimating Spontaneous Mutation Rates" Mutation Research (1993) pp. 187-189, vol. 292, No. 2.
Kato, T. et al., "Isolation and Characterization of Mutants of *Escherichia coli* Deficient in Induction of Mutations by Ultraviolet Light" Molecular & General Genetics (1977) pp. 121-131, vol. 156, No. 2.
Kenyon, C.J. et al., "DNA-damaging agents stimulate gene expression at specific loci in *Escherichia coli*" Proceedings of the National Academy of Sciences of the United States of America-Biological Sciences (1980) pp. 2819-2323. vol. 77, No. 5.
Kim, S.R. et al., "Roles of Chromosomal and Episomal dinB genes encoding DNA pol IV in Targeted and Untargeted mutagenesis in *Escherichia coil*" Molecular Genetics and Genomics (2001) pp. 207-215, vol. 266, No. 2.
Kim, S.R. et al., "Multiple pathways for SOS-induced mutagenesis in *Escherichia coli*: An overexpression of dinBydinP results in strongly enhancing mutagenesis in the absence of any exogenous treatment to damage DNA" Proc Natl Acad Sci USA (Dec. 1997) pp. 13792-13797, vol. 94, No. 25.

(Continued)

*Primary Examiner* — Albert Navarro
(74) *Attorney, Agent, or Firm* — Scully, Scott, Murphy & Presser, P.C.

(57) ABSTRACT

This disclosure provides methods and compositions for targeted mutagenesis of specific genes in a bacterial strain. By inducibly over-expressing error-prone polymerases such as Pol IV or Pol V in conjunction with nickase in a bacterial strain, and housing the targeted gene(s) on an episome or plasmid which contains one or more nickase recognition sequences, the targeted gene(s) can be selectively mutated at rates significantly greater than genes contained on the chromosome. The methods disclosed herein are useful for engineering desirable bacterial phenotypes and novel strains, including for example strains useful for treating or degrading waste and/or environmental contaminants, for optimizing bioprocesses, and for converting low-value feed-stock into value-added products.

22 Claims, 4 Drawing Sheets

(56) References Cited

OTHER PUBLICATIONS

Layton, J.C. et al., "Error-prone DNA polymerase IV is controlled by the stress-response sigma factor, RpoS, in *Escherichia coil*" Molecular Microbiology (2003) pp. 549-561, vol. 50, No. 2.

Lee, S. et al., "A Propionate-Inducible Expression System for Enteric Bacteria" Applied Environ Microbiology (Nov. 2005) pp. 6856-6862, vol. 71, No. 11.

Luria, S.E. et al., "Mutations of Bacteria From Virus Sensitivity to Virus Resistance" Genetics (May 29, 1943) pp. 491-511, vol. 28, No. 6.

Lynch, M.D. et al., "Broad host range vectors for stable genomic library construction" Biotechnol Bioeng (May 5, 2006) pp. 151-158, vol. 94, No. 1.

Sanders, L.H. et al., "Role of *Pseudomonas aeruginosa* dinB-Encoded DNA Polymerase IV in Mutagenesis" Journal of Bacteriology (Dec. 2006) pp. 8573-8585, vol. 188, No. 24.

Schlacher, K. et al., "Roles of DNA Polymerase V and RecA Protein in SOS Damage-induced Mutation" Chemical Reviews (2006) pp. 406-419, vol. 106, No. 2.

Smailus, D.E. et al.,"Constructing Larae DNA Segments by terative Clone Recombination" Syst Synth Biology (2007) pp. 139-144, vol. 1, No. 3.

Steinborn, G., "Uum Mutants of *Escherichia coli* K 12 Deficient in UV Mutagenesis" Molecular & General Genetics (1978) pp. 87-93, vol. 165, No. 1.

Stewart, F.M., "Fluctuation Tests: How reliable Are the Estimates of Mutation Rates?" Genetics (Aug. 1994) pp. 1139-1146, vol. 137, No. 4.

Uchida, K. et al., "Overproduction of *Escherichia coli* DNA Polymerase DinB (Pol IV) Inhibits Replication Fork Progression and is Lethal" Molecular Microbiology (2008) pp. 608-622, vol. 70, No. 3.

Urlacher, V.B. et al., "Microbial P450 Enzymes in Biotechnology" Applied Microbiology arid Biotechnology (2004) pp. 317-325, vol. 64, No. 3.

Rodriguez, C. et al., "Induction of a DNA Nickase in the Presence of Its Target Site Stimulates Adaptive Mutation in *Escherichia coli*" Journal of Bacterioiogy (Oct. 2002) pp. 5599-5608, vol. 184, No. 20.

Tompkins, J.D. et al., "Error-Prone Polymerase, DNA Polymerase IV, Is Responsible for Transient Hypermutation During Adaptive Mutation in *Escherichia coli*" Journal of Bacteriology (Jun. 2003) pp. 3469-3472, vol. 185, No. 11.

Gawel, D. et al., "A Novel Mutator of *Escherichia coil* Carrying a Defect in the dgt Gene, Encoding a dGTP Triphosphohydrolase" Journal of Bacteriology (Nov. 2008) pp. 6931-6939, vol. 190, No. 21.

McConnell Smith, A. et al., "Generation of a Nicking Enzyme that Stimulates Site-Specific Gene Conversion from the I-Anil LAGLIDADG Homing Endonuclease" Proc. Natl. Acad. Sci. USA (Mar. 31, 2009) pp. 5099-5104, vol. 106, No. 13.

International Search Report dated Dec. 26, 2011 issued in international Application No. PCT/US2011/028804.

Kuban, W. et al., "Mutator Phenotype Resulting from DNA Polymerase IV Overproduction in *Escherichia coil*: Preferntial Mutagenesis on the Lagging Strand" Journal of Bacteriology (Oct. 2005) pp. 8862-6866, vol. 187, No. 19.

Canitrot, Y. et al., "Overexpression of DNA Polymerase β in Cell Results in a Mutator Phenotype and a Decreased Sensitivity to Anticancer Drugs" Proc. Natl. Acad. Sci. USA (Oct. 1998) pp. 12586-12590, vol. 95.

Lee, S. et al., "Heterologous Protein Production in *Escherichia coli* Using the Propionate-Inducible pPro System by Conventional and Auto-Induction Method" Protein Expression and Purification (2008) pp. 197-203, vol. 61.

Gruber, D.F. et al., "Strict Regulation of Gene Exprest-lion From a High-Copy Plasmid Utilizing a Dual Vector System" Protein Expression and Purification (2008) pp. 53-57, vol. 60.

Tang, M. et al., "UmuD'2C is an Error-Prone DNA Poiymerase, *Escherichia coil* pol V" Proc. Natl. Acad. Sci. USA (Aug. 1999) pp. 8919-8924, vol. 96.

METHODS AND COMPOSITIONS FOR TARGETED MUTAGENESIS IN BACTERIA

CROSS REFERENCE TO RELATED APPLICATION

This application claims the benefit of priority from U.S. Provisional Application No. 61/314,828, filed on Mar. 17, 2010, the entire content of which is incorporated herein by reference.

STATEMENT REGARDING FEDERALLY SPONSORED RESEARCH OR DEVELOPMENT

This invention was made with Government support under Grant Number N00014-09-1-0234 awarded by the Office of Naval Research. The United States Government has certain rights in the invention.

FIELD OF THE DISCLOSURE

This disclosure generally relates to targeted mutagenesis in bacteria. More particularly, this disclosure provides methods and nucleic acid compositions for achieving targeted mutagenesis of specific genes in a bacterial strain, and the related bacterial strains.

BACKGROUND ART

There are two error-prone DNA polymerases of the Y-type polymerase family that have been studied extensively in *E. coli*: DNA polymerase IV (Pol IV) (Kenyon et al., *Proc Natl Acad Sci USA* 77(5), 2819-2823 (1980)) and DNA polymerase V (Pol V) (Kato et al., *Molecular & General Genetics* 156(2), 121-131 (1977); Steinborn et al., *Molecular & General Genetics* 165(1), 87-93 (1978)). Pol IV is part of the translesional DNA synthesis (TLS) pathway that allows for DNA damage repair. Pol IV greatly increases mutational activity in *E. coli* (Kim et al., *Proc Natl Acad Sci USA* 94(25), 13792-7 (1997)) and *P. aeruginosa* (Sanders et al., *Journal of Bacteriology* 188(24), 8573-8585 (2006)) when over-expressed. In fact, *E. coli* over-expressing Pol IV exhibits up to 200-fold higher mutational rates than cells not over-expressing Pol IV (Tompkins et al., *J. Bacteriology* 185(11), 3469-72 (2003)). More recently Pol IV has been shown to be lethal when over-expressed at very high levels (approximately 20 times more Pol IV than control cells), indicating that controlling the level of Pol IV is crucial to obtaining mutated genotypes (Uchida et al., *Molecular Microbiology* (2008)). There are approximately 250 copies of Pol IV in a single, unstressed *E. coli* cell (Kim et al., *Molecular Genetics and Genomics* 266(2), 207-215 (2001)).

The level of Pol V in unstressed *E. coli* is far lower than for Pol IV: approximately 5 copies per cell (Fuchs et al., *DNA Repair and Replication* 69, 229-264 (2004)). Pol V is encoded by UmuDC (Fuchs et al., *DNA Repair and Replication* 69, 229-264 (2004)). The role of Pol V is perhaps less clear than for Pol IV, but it is clear that Pol V also functions as part of the TLS system (Schlacher et al., *Chemical Reviews* 106(2), 406-419 (2006)). Pol V has a requirement for ATP and damaged DNA in order to be functional (Schlacher et al., *Chemical Reviews* 106(2), 406-419 (2006)) and is active in repairing DNA damage caused by complete replication blocks: either from UV light, polycyclic hydrocarbons or other mutagenic agents (Fuchs et al., *DNA Repair and Replication* 69, 229-264 (2004)). In order to replicate damaged DNA, Pol V requires the active form of RecA protein to be present (Schlacher et al., *Chemical Reviews* 106(2), 406-419 (2006)). Pol V requires RecA for its own activation both transcriptionally and post-transcriptionally as well as during DNA replication (Fujii et al., *J. Molecular Biology* 341(2), 405-17 (2004)).

Both Pol IV and Pol V are implicated in the SOS response of *E. coli*. As part of that system the error-prone polymerases have requirements for the β clamp subunit of the replicative polymerase Pol III (Burnouf et al., *J. Molecular Biology* 335(5), 1187-1197 (2004)). Without the β clamp, neither polymerase can push replication beyond a stalled replication fork (Fujii et al., *J. Molecular Biology* 341(2), 405-417 (2004b); Wagner et al., *Embo Reports* 1(6), 484-488 (2000)). However, both Pol IV and Pol V are able to facilitate DNA replication in vitro without the β clamp (Fujii et al., *Journal of Molecular Biology* 341(2), 405-417 (2004); Kim et al., *Proc Natl Acad Sci USA* 94(25), 13792-7 (1997)). Pol IV is controlled at least partially by the sigma factor RpoS in *E. coli* (Layton et al., *Molecular Microbiology* 50(2), 549-61 (2003)).

Both Pol IV [aka DinB] and Pol V have been linked to high non-targeted mutation rates in several species. Over-expression of Pol IV (or Pol V) in *P. aeruginosa* results in a mutator phenotype that can confer resistance to bactericidal agents.

The technique of directed evolution has been established as a method for developing bacterial and yeast strains capable of degrading recalcitrant compounds such as polyaromatic hydrocarbons and chlorinated solvents (Ang et al., *Abstracts of Papers of the American Chemical Society* 229, U223-U223 (2005a); Ang et al., *Enzyme and Microbial Technology* 37(5), 487-496 (2005b); Diaz et al., *Microbiology and Molecular Biology Reviews* 65(4), 523 (2001); Furukawa, *Bioscience Biotechnology and Biochemistry* 70(10), 2335-2348 (2006); Urlacher et al., *Applied Microbiology and Biotechnology* 64(3), 317-325 (2004)). Typically the technique involves the mutation of specific genes and the subsequent evolution of those genes in chemostat culture under low levels of selective pressure from the contaminant of interest or with the contaminant of interest as sole carbon source. This approach though is cumbersome and slow.

SUMMARY OF THE DISCLOSURE

This disclosure is directed to methods and compositions for achieving targeted mutagenesis of specific nucleic acid(s) in a bacterial strain. By expressing an error-prone polymerase in a controlled manner in a host bacterial strain, in conjunction with a nickase, and by placing a targeted nucleic acid on an episome or plasmid which contains one or more nickase recognition sequences, the targeted nucleic acid can be selectively mutated at rates significantly greater than genes on the chromosome of the bacterial strain.

In one aspect, this disclosure provides a method of generating mutations within a target DNA. The method utilizes a host bacterial strain, which contains a nucleic acid coding for an error-prone DNA polymerase under control of an inducible transcriptional regulatory region, a nucleic acid coding for a nicking enzyme, and a vector carrying a target DNA which is placed in proximity to at least one recognition site of said nicking enzyme. Such strain is cultured under conditions that permit the expression of the error-prone DNA polymerase and the nicking enzyme, thereby generating mutations within said target DNA.

In some embodiments, the nucleic acid coding for the nicking enzyme is also under control of an inducible transcriptional regulatory region. In one embodiment, the nucleic acid coding for the error-prone DNA polymerase and the nucleic acid coding for the nicking enzyme are under control of a single inducible transcriptional regulatory region. In another embodiment, the nucleic acid coding for the error-prone DNA polymerase and the nucleic acid coding for the nicking enzyme are under control of separate inducible transcriptional regulatory regions.

Error-prone DNA polymerases suitable for use herein include bacterial DNA polymerase IV (Pol IV) or DNA polymerase V (Pol V). In specific embodiments, the error-prone DNA polymerase employed herein is *E. coli* or *Pseudomonas aeruginosa* Pol IV or Pol V.

Nicking enzymes suitable for use herein include the nickase encoded by gene II of bacteriophage f1, the nickase encoded by the traI gene native to the F' episome, among others.

In some embodiments, an inducible regulatory region that regulates one of the genes lacZ, prpB, and araB is utilized. In one embodiment, the propionate-inducible pPro regulatory region is employed. In other embodiments, a stress promoter of a bacterial species is used to effect controlled expression. Examples of stress-induced promoters include those that regulate production of various sigma factors such as $\sigma^{19}$, $\sigma^{24}$, and $\sigma^{54}$, and those that are sensitive to an environmental or organic contaminant or pollutant such as the sep controller region from *P. putida*.

A mutator expression cassette or unit, composed of an inducible regulatory region, operably linked to a gene encoding an error-prone DNA polymerase, optionally followed by a gene encoding a nicking enzyme, can be introduced to a host bacterial strain by standard methods, e.g., by transformation or conjugation. Such expression cassette can be maintained in the host strain by way of a plasmid, an episome, or integrated into the bacterial chromosome. When both an error-prone DNA polymerase and a nicking enzyme are inducibly expressed, the gene encoding the error-prone DNA polymerase and the gene encoding the nicking enzyme can be placed under a single inducible regulatory region, introduced into a host strain and maintained in the host strain together; or alternatively, the two genes can be placed under separate inducible regulatory regions, and introduced and maintained together or independently.

The targeted mutagenesis approach disclosed herein can be applied to mutate any nucleic acid molecules of interest, including prokaryotic genes and eukaryotic genes, as well as libraries of prokaryotic or eukaryotic genes which allows for generating a library of mutated genes. A target nucleic acid, either a single gene or including multiple genes, can be placed on a plasmid or episome, and introduced into a host bacterial strain using standard techniques.

In specific embodiments, a target nucleic acid is placed on a plasmid or episome in proximity to one or more nucleotide recognition sites of a nicking enzyme. In one embodiment, the site is defined by the nucleotide sequence, 5'-GTTGTTC-CAGTTTGGAACAAGAGTCCACTATTAAAGA-3' (SEQ ID NO: 50), which is recognized the nickase encoded by geneII.

As disclosed herein, the bacterial strain, which contains a nucleic acid coding for an error-prone DNA polymerase under control of an inducible transcriptional regulatory region, a nucleic acid coding for a nicking enzyme, and a vector carrying a target DNA placed in proximity to at least one recognition site of said nicking enzyme, is cultured under controlled growth conditions and induced to allow for the expression of the mutator gene (such as Pol IV and nickase), thereby generating mutations in the target DNA. Mutants can be selected using known techniques, e.g., based on selectable phenotypes.

In other aspects of the invention, the related vectors and host strains are packaged into a kit, which is useful for the skilled artisan to perform the mutagenesis method disclosed herein. The resulting strains, including strains having desirable phenotypes, are also provided.

DETAILED DESCRIPTION

Figure 1:
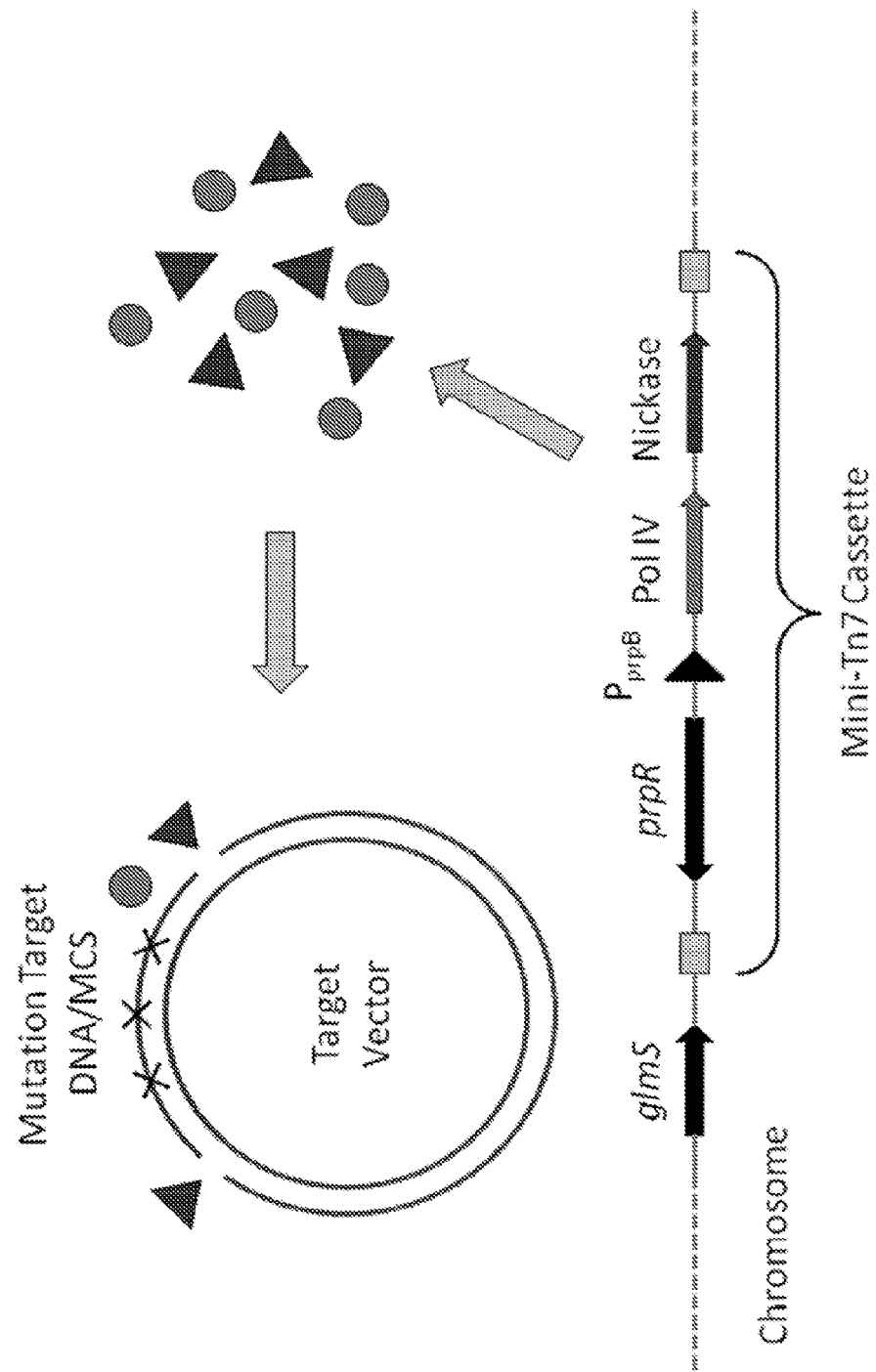
FIG. 1. One embodiment of the disclosed system for tightly controlled in-cell targeted mutagenesis is graphically depicted. Genes dinB and gII, encoding DNA Polymerase IV and the GeneII nickase, respectively, are placed under control of a propionate inducible promoter and are chromosomally inserted by means of a mini-Tn7 system downstream of the glmS gene and in a non-coding region of DNA. Also included in this mini-Tn7 cassette is the gene prpR involved in propionate inducible gene regulation. When induced with propionate, cells produce DNA Polymerase IV (circles), and GeneII nickase (triangles). The nickase recognizes sites flanking a target region of DNA on our mutation target plasmid and causes DNA single strand breaks at these sites. Upon target vector replication, these single strand breaks can result in replication fork collapse and DNA double strand breaks. Repair by homologous recombination involving overexpressed DNA Polymerase IV can then result in mutations within the target region of our mutation target vector.
Figure 2:
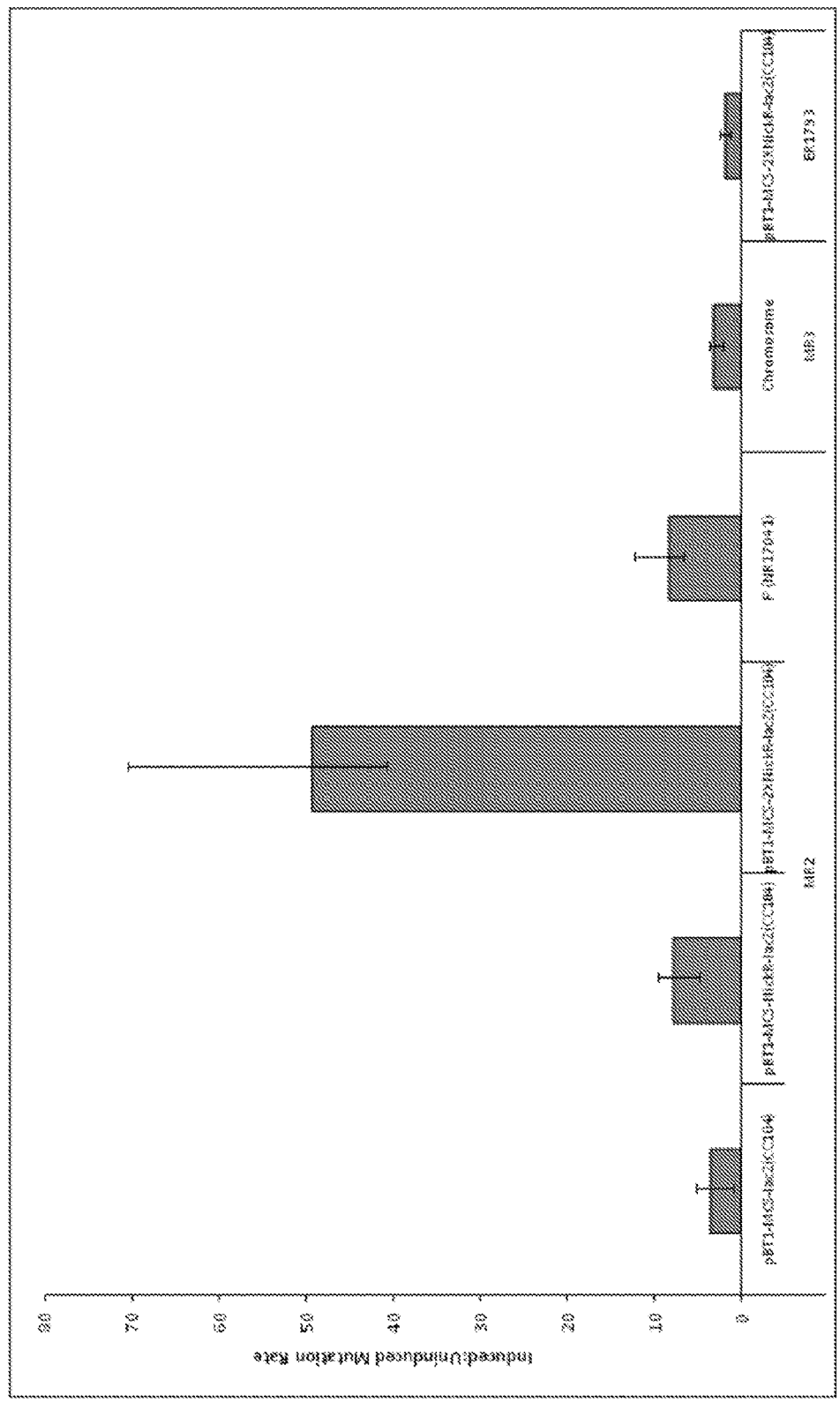
FIG. 2. Ratios of estimated mutation rates at induced conditions (5 mM [propionate]) to mutation rates at uninduced conditions (0 mM [propionate]). Mutation rate is defined as the probability of observing the specified mutation per cell per generation. Mutation rates are for the reversion the lacZ (CC104) by a specific G:C→T:A transversion mutation. This allele was located on mutation target vectors pBT1-MCS-lacZ(CC104), pBT1-MCS-NickR-lacZ(CC104), and pBT1-MCS-2XNickR-lacZ(CC104) with 0, 1, and 2 recognition sites for the GeneII nickase, respectively, as well as on the F' episome of Strain NR17041 (Gawel et al., *Journal of Bacteriology* 190(21), 6931-9 (2008)), which was nicked at a single site by its self-encoded TraI nickase, and on the chromosome in strain MR3 with no known nearby nick sites. Strain MR3 was also transformed with pBT1-MCS-2XNickR in order to make it nearly isogenic with strain MR2 constructs. The Ratio of induced:uninduced mutation rate was also estimated on pBT1-MCS-2XNickR-lacZ(CC104) in control strain ER1793, lacking the disclosed system for over-expression of DinB or the GeneII nickase. 95% confidence intervals were generated for these mutation rate ratios using the method of Russell and March (*Environ Mol. Mutagen.* DOI: 10.1002/em.20636, 2010).
Figure 3:
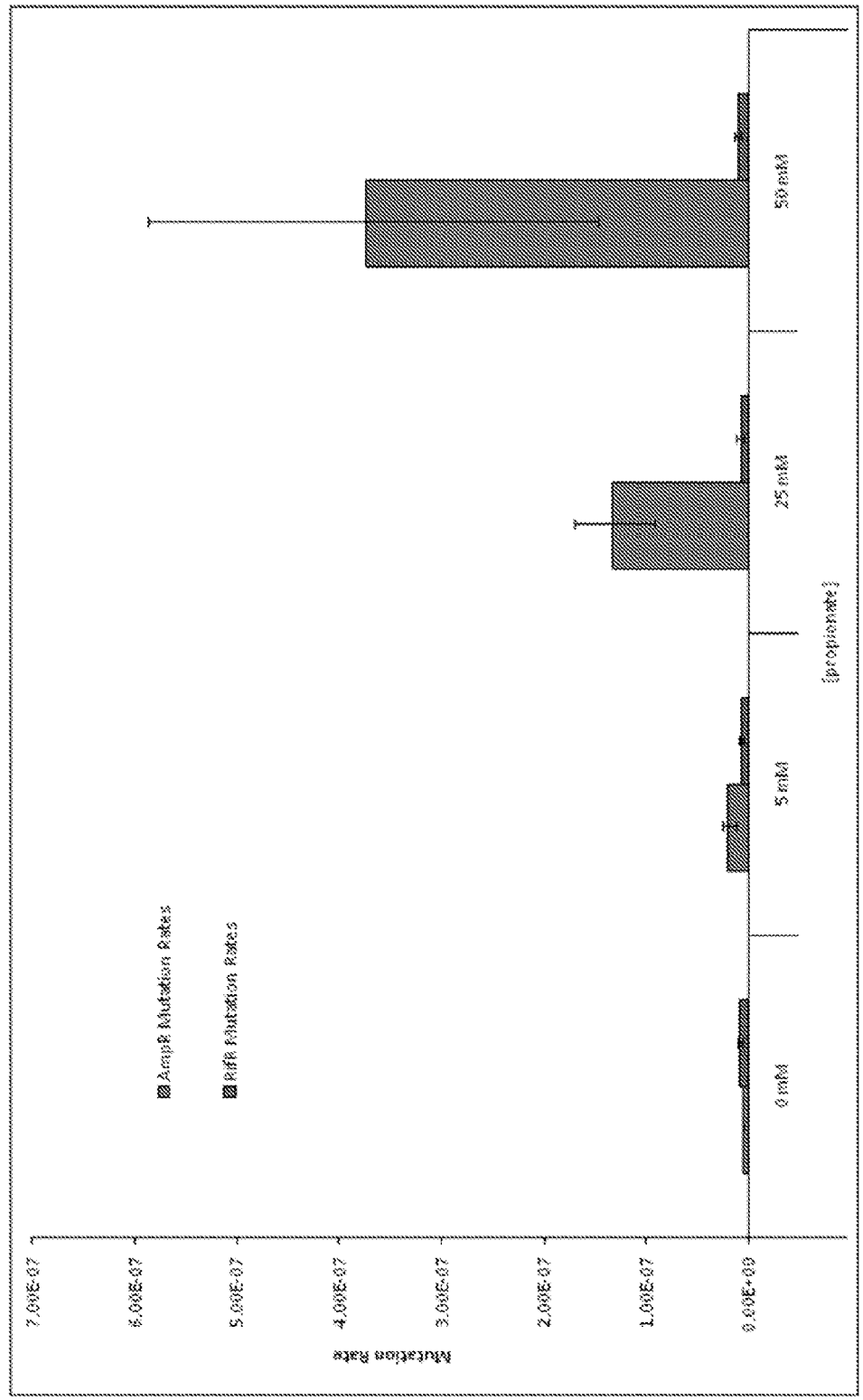
FIG. 3. Mutation rates estimated in strain MR2 carrying plasmid pRapt2-Kan-bla at 0, 5, 25, and 50 mM propionate concentrations. Rates shown are for reversions of the bla allele on mutation target vector pRapt2-Kan-bla conferring ampicillin resistance, and for mutations of the rpoB gene on the chromosome conferring rifampicin resistance. Mutation rate is defined as the probability of observing the specified mutation per cell per generation. 95% confidence intervals were generated as described in Foster (Methods Enzymol 409, 195-213, 2006).
Figure 4:
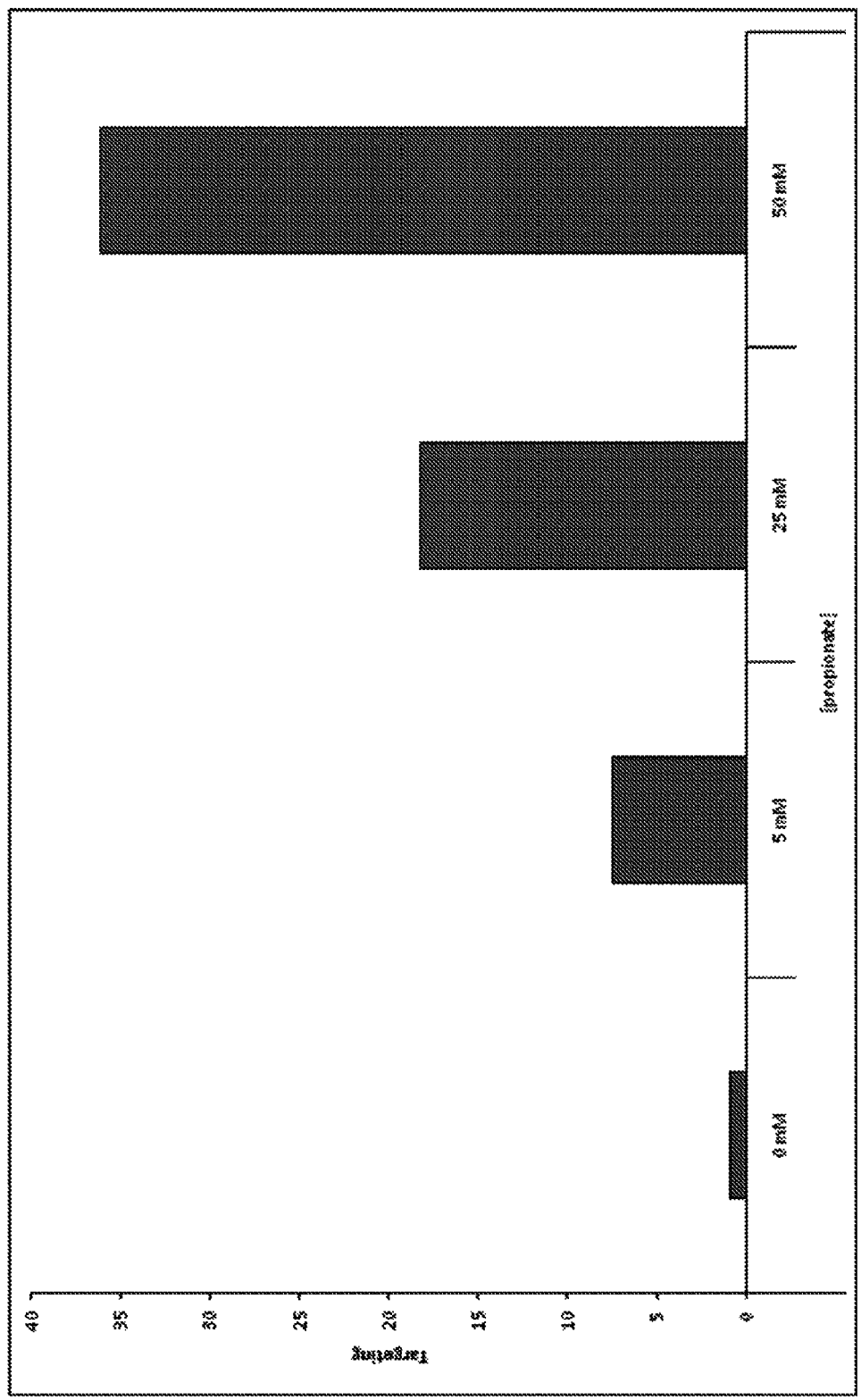
FIG. 4. Targeting of mutation to the bla allele on pRapt2-Kan-bla by the system disclosed herein at different concentrations of propionate. The mutation rates for reversions on mutation target vector pRapt2-Kan-bla conferring ampicillin resistance in strain MR2 at different propionate concentrations were normalized to the mutation rates for reversions on pRapt2-Kan-bla in control strain ER1793 under the same conditions. The mutation rates for the chromosomal rpoB gene, conferring rifampicin resistance, in strain MR2 at different propionate concentrations were normalized to the mutation rates for the rpoB gene in control strain ER1793 under the same conditions. Finally, targeting was calculated as the quotient of the normalized target vector mutation rates divided by normalized chromosomal mutation rates. This method accounts for differences in copy number and differences between the mutation target genes (Camps et al., *Proc Natl Acad Sci USA* 100(17), 9727-32, 2003).

This disclosure is directed to methods and compositions for achieving targeted mutagenesis of specific genes in a bacterial strain, and to the related bacterial strains. By expressing an error-prone polymerase in a controlled manner in a bacterial strain, in conjunction with a nickase, and by placing a targeted gene on an episome or plasmid which contains one or more nickase recognition sequences, the targeted gene can be selectively mutated at rates significantly greater than genes on the chromosome of the bacterial strain.

The in-cell localized mutagenesis approach disclosed herein provides a significantly increased rate of mutation within a target gene under predefined conditions, and permits development of bacterial strains with great diversity and desirable bacterial phenotypes. For example, bacterial strains can be developed that sense a particular stressor and respond with hyper-mutation rates resulting in rapid adaptation to the stressor. These strains are also referred herein as "Rapidaptor" strains.

The in-cell localized mutagenesis approach disclosed herein can be used to develop novel strains for treating or degrading waste and/or environmental contaminants, for optimizing bioprocesses, for converting low-value feedstock into value added products or for any application where mutation may play a role. This approach also allows for the study of how changes in a gene or gene system can affect the manner by which different organisms interact. For example, when two or more types of microorganisms are grown together, the mutagenesis approach disclosed herein allows for mutation of a gene system in one of these organisms such that the effect of the mutation(s) on the inter-organism interactions or single organism reactions can be studied.

The various features of the targeted in-cell mutagenesis approach of this invention are further described below.

Mutator Genes

The targeted mutagenesis approach of this disclosure is based on a controlled expression of at least one mutator gene in a host bacterial strain.

As used herein, a "mutator gene" encodes an error-prone DNA polymerase. In specific embodiments, the error-prone DNA polymerase is a bacterial DNA polymerase IV (Pol IV) or DNA polymerase V (Pol V). Pol IV and Pol V have been linked to high mutation rates in several bacterial species. Under conditions of high stress such as osmotic pressure or DNA damage, these polymerases are up-regulated (both transcriptionally and through regulatory proteins) and result in rapid rates of mutation via single base mutations as well as insertion and deletion mutations.

Genes encoding Pol IV and Pol V have been cloned from various bacterial species including, for example, *E. coli* and *Pseudomonas aeruginosa*, the sequences of which are available to those skilled in the art. See, e.g., RefSeq NC_000913 (250,898 . . . 251,953), (1,229,990 . . . 1,230,409), and (1,230,409 . . . 1,231,677) representing the RefSeq accession numbers for *E. coli* dinB, umuD, and umuC (Pol IV and V) with the chromosomal beginning and ending positions of these genes indicated in parentheses; and NC_002516 (1,007,950 . . . 1,008,999), representing the RefSeq accession number of *P. aeruginosa* dinB (Pol IV). In some embodiments, the error-prone polymerase (such as Pol IV or Pol V) that is expressed in a controlled manner in a host strain is originated from the host strain, i.e., identical in sequence with the native error-prone DNA polymerase of the host strain. In other embodiments, the error-prone DNA polymerase (such as Pol IV or Pol V) that is expressed in a controlled manner in a host strain for purposes of targeted mutagenesis is derived from a different bacterial species or strain, but shares substantial sequence and structural homology with the native enzyme of the host strain and also functions in the host strain. For example, while it may be preferred to inducibly express Pol IV of *E. coli* in an *E. coli* strain, it is also possible to inducibly express *E. coli* Pol IV in a *Pseudomonas* host strain or *Pseudomonas* Pol IV in an *E. coli* strain.

In addition to an error-prone polymerase, the target mutagenesis approach disclosed herein also employs, in some embodiments, controlled expression of a gene encoding a nicking enzyme. It has been recognized in the course of this invention that the rates of mutations within a target gene can be significantly enhanced by placing one or more nicking enzyme recognition sites near the target gene. Without wishing to be bound by any particular theory, it is believed that these recognition sites are acted upon by the nicking enzyme, causing DNA single strand breaks at these sites which can result in collapse of the replication fork during replication and DNA double strand breaks. Repair of these breaks by homologous recombination involving an error-prone DNA polymerase then results in mutations within the target gene.

An example of nicking enzymes suitable for use herein is the nickase encoded by gene II of bacteriophage f1; GenBank V00606 (6,006 . . . 6,407, 1 . . . 831). Another example of a nickase is the traI encoded nickase native to the F' episome which creates a persistent nick at oriT (Rodriguez et al., *Journal of Bacteriology* 184(20), 5599-608 (2002)). Several plasmids that utilize rolling circle replication also encode nickases which provide a single strand break necessary to initiate replication. Homing endonucleases, such as I-SceI (Chen and Zhao, *Nucleic Acids Research* 33(18), e154 (2005)), which cause double strand breaks directly at a target sites are suitable as well provided that they are suitably regulated to allow for some intact copies of mutation target plasmids as templates for double strand break repair by homologous recombination.

Controlled Expression of Mutator Genes from Inducible Promoters

In order to achieve controlled expression of a mutator gene, the mutator gene is placed under control of an inducible regulatory region in a host strain. Where both an error-prone DNA polymerase and a nicking enzyme are utilized, the gene encoding the error-prone DNA polymerase and the gene encoding the nicking enzyme can be placed under separate inducible regulatory regions, or placed under a single inducible regulatory region.

By "an inducible regulatory region" it is meant a transcriptional regulatory region which includes an inducible promoter, and where appropriate, any additional transcriptional elements such as an enhancer sequence. Inducible promoters are off (i.e., remain inactive) unless a molecule (called an inducer) is present which allows for gene expression. Enhancers are cis-acting elements of DNA, usually about from 10-300 bp, which act on a promoter to increase its transcription.

Many inducible promoters functional in bacterial strains are known in the art and are suitable for use in this invention.

Examples of inducible promoters suitable for use herein include those that regulate the genes lacZ, prpB, and araB which produce protein products responsible for metabolism of lactose, propionate and arabinose, respectively, and are inducible by these or Isopropyl β-D-1-thiogalactopyranoside (IPTG) in the case of the lacZ promoter.

In one specific embodiment, controlled, inducible expression of a mutator gene is achieved by using the propionate-inducible pPro system, which has been described in, e.g., Lee and Keasling, *Applied Environmental Microbiology* 71(11): 6856-6862 (2005), and Lee and Keasling, *Protein Expression & Purification* 61: 197-203 (2008), incorporated herein by reference. In this pPro system, the inducible transcriptional regulatory region includes the prpBCDE promoter ($P_{prpB}$) responsible for expression of the propionate catabolic genes (prpBCDE), and prpR encoding the positive regulator of this promoter, which can be obtained or derived from various bacterial species (such as *E. coli* or *Samonella enterica*). The pPro system provides highly regulatable expression of cloned genes over a wide range of propionate concentrations, and strong expression at high propionate concentrations (up to 1500-fold induction), and exhibits negligible basal expression in the presence of glucose contained in the medium.

In another specific embodiment, controlled, inducible expression of a mutator gene is achieved by using the dual plasmid expression system (pDual), which has been described by Gruber et al., *Protein Expression & Purification* 60: 53-57 (2008), incorporated herein by reference. According to this pDual system, the mutator gene is operably linked to the lac promoter and can be placed in a plasmid (including a high-copy plasmid), an episome, or integrated in the chromosome in a host strain. A series of plasmids with varying copies of the $lacI^q$ gene are constructed to permit titration of the amount of the LacI protein expressed in the host strain and selection of a level of regulation that optimizes inducible expression of the mutator gene from the lac promoter, thereby achieving tight regulation of the expression of the mutator gene.

In other embodiments, inducible expression of a mutator gene is achieved by using a stress-induced promoter. Stress promoters are well-characterized for several bacterial species such as *E. coli* and include several sigma factors as well as central metabolic, anabolic and motility genes. Examples of stress-induced promoters include those that regulate production of various sigma factors such as $\sigma^{19}$, $\sigma^{24}$, and $\sigma^{54}$ which in turn regulate genes in response to ferric stress, extracytoplasmic, and nitrogen limitation respectively.

In specific embodiments, the stress inducible promoter is a promoter sensitive to an environmental or organic contaminant or pollutant. For example, the quorum sensing system (autoinducer 2) provides a host of promoters sensitive to external stimuli. In *Pseudomonas*, there are genes associated with the degradation of various contaminants and with the resistance of various antimicrobials that have been sequenced and whose transcriptional regulation is understood. For example, the sep controller region from *P. putida* is activated under several different organic pollutants and has been utilized in the development of a biosensor for benzene, toluene, ethylbenzene, and all three isomers of xylene (BTEX), naphthalene, and complex mixtures of aliphatic and aromatic hydrocarbons (Phoenix et al., *Environmental Microbiol* 5(12): 1309-27 (2003)). The sep promoter region from *P. putida* has been combined with the luxCDABE operon from *Photorhabdus luminescens* for the detection of available contaminants in soil. Similarly, the multidrug efflux pump system of *P. aeruginosa* is activated through ligand binding to the MexZ operon (Morita et al., *J. Bacteriol* 188(5): 1847-55 (2006)), and the tod operon of *P. putida* is activated by BTEX and trichloroethylene (Applegate et al., *Appl Environ Microbiol* 64(7): 2730-5 (1998); Shingleton et al., *Appl Environ Microbiol* 64(12): 5049-52 (1998)). In all cases, a broad range of potential degradation targets activate expression of a single operon or gene.

Expression of an error-prone polymerase in response to stress or a pollutant allows mutating exposed strains at a rate consistent with the amount of contaminant, resistance to and metabolism of the contaminant occurs more rapidly when it is most needed. In essence, the mutagenesis approach disclosed herein allows for the development of an inducible rapidly adaptable bacterial strain that can be exogenously stimulated to mutate at a controllable rate, and a condition-driven rapidly adaptable bacterial strain that can be stimulated to mutate by an external stressor. Such rapidly adapting strains can be used for the biodegradation of environmental contaminants or converting low value feedstock into value-added products.

Introduction of a Mutator Expression Cassette into a Host Strain

A mutator expression cassette, composed of an inducible regulatory region, operably linked to a mutator gene (such as the gene encoding Pol IV), can be introduced to a host bacterial strain by standard methods, e.g., by transformation or conjugation. Such expression cassette can be maintained in the host strain by way of a plasmid, an episome, or integrated into the bacterial chromosome.

In specific embodiments, the mutator expression cassette is integrated into the chromosome of a host strain. Chromosomal integration in bacteria can be achieved using methods well documented in the art, including for example, the mini Tn7 gene insertion system as described by, e.g., Bao et al., *Gene* 109(1): 167-8 (1991); Choi et al., *J Microbiol Methods* 64(3):391-7 (2006); Choi et al., *Nat Protoc* 1(1):1708 (2006); Choi et al., *Nat Protoc* 1(1):153-61 (2006), all of which are incorporated herein by reference. By inserting a single copy of either Pol IV or Pol V into the chromosome under control of an inducible promoter, any possible stress caused by plasmid maintenance can be avoided. Further, lower copies of Pol IV or Pol V can minimize or completely avoid growth retardation and senescence.

To achieve complete controlled expression of error-prone DNA polymerases, in some embodiments, the endogenous gene(s) in the host strain encoding the native error-prone polymerases can be inactivated or knocked out. This can be accomplished by using standard methods.

In embodiments where both an error-prone DNA polymerase and a nicking enzyme are inducibly expressed, the gene encoding the error-prone DNA polymerase and the gene encoding the nicking enzyme can be placed under a single inducible regulatory region and introduced into a host strain and maintained in the host strain together. Alternatively, the two genes can be placed under separate inducible regulatory regions, and can be introduced and maintained independently (by way of a plasmid, episome or integrated in the chromosome), or introduced and maintained together, e.g., through one single vector.

Target Nucleic Acids to be Mutated

The targeted mutagenesis approach disclosed here can be used to mutate any nucleic acid molecules of interest, including prokaryotic genes and eukaryotic genes, as well as libraries of prokaryotic or eukaryotic genes which allows for generating a library of mutated genes. Eukaryotic genes can be in the form of a cDNA or genomic DNA with or without introns. Examples of target genes of interest include, but are not limited to, the β-lactamase gene or inactive alleles of this gene capable of reversion to an active form, the β-galactosidase or inactive alleles of this gene capable of reversion to an active form, cel5A, cel6B, bglC, genes encoding antimicrobial proteins, and green fluorescent protein (GFP).

Target nucleic acids, which can be a single gene or can include multiple genes, operons and/or intergenic regions, can be placed on a plasmid or episome, and introduced into a host bacterial strain using standard techniques. A variety of plasmids are available in the art and can be used as the carrier of a target nucleic acid(s), so long as the plasmid can replicate in the host bacterial strain and contains an appropriate selection marker gene.

In specific embodiments, a target nucleic acid is placed on a plasmid or episome in proximity to one or more nucleotide recognition sites of a nicking enzyme. It has been recognized in accordance with this invention that the presence of one or more recognition sites of a nicking enzyme near the target nucleic acid enhances the mutation rates within the target nucleic acid as well as the target specificity.

By "target specificity" it is meant that the increased mutation rate as a result of the expression of an error-prone DNA polymerase is specifically directed to the target nucleic acid of interest, as opposed to genes on the bacterial chromosome. For example, using the targeted mutagenesis system disclosed herein, a target nucleic acid can be selectively mutated at rates at least 10 fold, 25 fold, 50 fold, 75 fold, or even 100 fold greater than genes on the chromosome.

By "proximity", it is meant that the target gene is placed within 300 bp, 200 bp, 100 bp, 50 bp, 25 bp or less of one or more nucleotide recognition sites of a nicking enzyme. In one embodiment, one recognition site of a nicking enzyme is placed in proximity 5' or 3' to the target nucleic acid. In another embodiment, two recognition sites of a nicking enzyme are placed in proximity 5' and 3' to the target nucleic acid, i.e., the target nucleic acid is flanked by the two sites.

An illustrative example of a nicking enzyme is the nickase encoded by geneII. The nickase recognition site is defined by the nucleotide sequence, 5'-GTTGTTCCAGTTTGGAACAAGAGTCCACTATTAAAGA-3' (SEQ ID NO: 50). In specific embodiments, a target nucleic acid is flanked by this nickase recognition site, as well as by 5 repeated Chi sequences (5'-GCTGGTGG-3', SEQ ID NO: 51) on either side.

In other embodiments, a target nucleic acid is placed on an episome, such as an F' episome, which contains one or more native recognition site of a nicking enzyme. It is preferable that the target nucleic acid is placed in proximity to such recognition site(s) on the episome to improve target specificity.

Culture, Induction and Selection

The targeted mutagenesis method is achieved by providing a host bacterial strain, which includes, e.g., by way of transformation, a first vector (in the form of a plasmid, episome, or an integrative vector leading to the integration into the chromosome) containing a nucleic acid coding for an error-prone DNA polymerase under control of an inducible regulatory region, and also includes a second vector (in the form of a plasmid or episome) carrying a target nucleic acid. In specific embodiments, the first vector also includes a nucleic acid encoding a nicking enzyme, and the target nucleic acid in the second vector is placed in proximity to one or more recognition sites of the nicking enzyme.

The bacterial strain is cultured under controlled growth conditions, and at an appropriate time (e.g., once the cell density reaches a desirable level), is induced to allow for the expression of the mutator gene (such as Pol IV and nickase). The strain is cultured under the inducing conditions for a desirable period of time to allow for generation and accumulation of mutations in the target nucleic acid.

Mutants can be selected based on selectable phenotypes (e.g., acquired ability to degrade or metabolize a compound, resistance to an antibiotic, among others). Alternatively, the mutated target vectors can be recovered from the bacterial strains, and target nucleic acids containing a desirable mutation(s) can be screened and selected in a separate in vitro or cellular system. Sequencing analysis can also be performed to identify the nucleotide changes in the target nucleic acid.

Host Bacterial Strains

The targeted mutagenesis approach of this disclosure can be accomplished using any gram negative bacteria or gram positive strains as host. Examples of gram negative bacteria include but are not limited to, *Escherichia* (e.g., *E. coli*), *Salmonella* (e.g., *Salmonella typhimurium*), *Shigella*, *Pseudomonas* (e.g., *Pseudomonas aeruginosa*), *Moraxella* (e.g., *Moraxella catarrhalis*), *Helicobacter* (*Helicobacter pylori*), *Klebsiella* (e.g., *Klebsiella pneumonia*), acetic acid bacteria, cynobacteria, green sulfur bacteria, and green nonsulfur bacteria. Examples of gram positive bacteria include species of *Bacillus* and *Lactobacillus*.

In specific embodiments, strains of *E. coli* or strains of *Pseudomonas aeruginosa* are used as host strains for targeted mutagenesis.

Vectors, Strains and Kits

The various vectors and strains described above can be provided and packaged in a kit for implementing the targeted mutagenesis method disclosed herein. These vectors, strains and kits are also parts of this invention.

EXAMPLES

The present description is further illustrated by the following examples, which should not be construed as limiting in any way. The contents of all cited references (including literature references, issued patents, and published patent applications as cited throughout this application) are hereby expressly incorporated by reference.

Example 1

This Example describes the general materials and methods utilized in certain exemplary experiments. The results of these experiments showed that when Pol IV was integrated into the chromosome of *E. coli* and overexpressed using an inducible promoter, the mutation rate for a target gene placed on an F' episome was about 100 times greater for the same target gene placed on the chromosome, where mutation rate is defined as the probability of observing a specific mutation event per cell per generation (Foster, *Journal of Bacteriology* 186(15) (2004)).

Plates, Media, and Stock Solutions.

For preparation of M9 agar plates, 11.3 g of Difco™ M9 Minimal Salts, 5× (Becton, Dickinson and Company) was dissolved in distilled water (dH$_2$O) and brought to a final volume of 200 ml. 100 ml was then poured into each of two 500 ml bottles and autoclaved 20 minutes to sterilize. 7.5 g of Bacto™ Agar (Becton, Dickinson and Company) was mixed with 400 ml dH$_2$O in two separate 500 ml bottles and also autoclaved 20 minutes to sterilize. When sterile, a bottle of agar and water was added to each M9 salts bottle and the total volume was brought to 500 ml with sterile dH$_2$O. M9 plates were supplemented with 1 ml of sterile 1M MgSO$_4$, 50 µl of sterile 1M CaCl$_2$, and 125 µl of 0.2 µm filter sterilized 10 mg/ml Thiamine HCl. For preparation of M9 lactose (M9 lac) plates, 10 ml of 0.2 µm filter sterilized 20% α-lactose was added per 500 ml bottle and 10 ml of 0.2 μm filter sterilized 20% D-glucose was added per 500 ml bottle for the preparation of M9 glucose (M9 glu) plates. M9 glucose medium was prepared in the same fashion except without the addition of agar.

50 mg/ml ampicillin (Shelton Scientific), 10 mg/ml kanamycin (EMD Chemicals), 10 mg/ml streptomycin (CalBiochem), 10 mg/ml Thiamine HCl (Research Organics), 20% L-glucose, and 20% α-lactose (J. T. Baker) were prepared with MilliQ water and then filtered with a 0.2 μm filter to sterilize. 34 mg/ml chloramphenicol (VWR International) was prepared in 95% ethanol (Mallinckrodt Chemicals). 5 M propionate (Alpha Aesar), 1 M $MgSO_4$ (Fisher Scientific), 1 M $CaCl_2$ (J. T. Baker), 1 M $KH_2PO_4$ (BDH Chemicals), 1 M $K_2HPO_4$ (J. T. Baker) and Difco™ LB Broth, Miller (Luria-Bertani) (Becton, Dickinson and Company) were prepared by dissolving chemicals in $dH_2O$ and autoclaving 20 minutes to sterilize. 66 mM pH 7.2 phosphate buffer was made by combining 7.1 ml 1 M $KH_2PO_4$ and 17.9 ml 1 M $K_2HPO_4$, bringing the solution to a final volume of 379 ml with $dH_2O$, and autoclaving 20 minutes to sterilize. LB plates were prepared in a similar fashion to LB medium except that 7.5 g of Bacto™ Agar (Becton, Dickinson and Company) was added per 500 ml before autoclaving. Antibiotics and supplements were added to plates and spread with a sterile spreader prior to plating bacteria. Unless otherwise specified, final antibiotic concentrations used were 100 μg/ml ampicillin (amp100), 25 μg/ml kanamycin (kan25), 25 μg/ml chloramphenicol (cm25), and 10 μg/ml streptomycin (str10). All primers were ordered through IDTDNA.

Bacterial Strain and Plasmid Construction

Plasmid pPro30 (developed in Jay Keasling's laboratory, Addgene plasmid 17809) was used for cloning and controlled overexpression of dinB (Lee et al., *Applied Environ Microbiology* 71(11), 6856-62 (2005)). First, dinB was amplified from chromosomal DNA isolated from strain ER1821 (New England Biolabs) using primers 1 and 2 then re-amplified adding restriction sites, a ribosomal binding site (RBS) and 5' untranslated region (5' UTR) with primers 3 and 4. All DNA amplifications were performed using the high fidelity Phusion DNA polymerase (New England Biolabs) on an iCycler™ Thermal Cycler (BIO-RAD) unless otherwise noted. Amplified dinB was digested with SadI and XbaI and ligated into the multiple cloning site (MCS) of pPro30 digested with the same enzymes. The sequences of dinB was verified from purified plasmid DNA after cloning using sequencing primers 5, 6, 7, and 8. Cloning steps were performed in *E. coli* strain DH5α made competent using the Inoue Method for Preparation and Transformation of Competent *E. coli*: "Ultra-Competent" Cells (Sambrook et al., *Molecular cloning: a laboratory manual*. Cold Spring Harbor Laboratory Press 3rd ed. (2001)). Other strains used were made competent using a method for One-step preparation of competent *Escherichia coli* unless otherwise noted (Chung et al., *Proc Natl Acad Sci USA* 86(7), 2172-5 (1989)). Plasmid DNA was purified using a QIAprep® Spin Miniprep Kit (Quiagen). Digested DNA was purified by TAE agarose gel electrophoresis followed by extraction and purification using a Nucleospin® Extract II kit (Machery-Nagel) prior to ligation using T4 DNA ligase (Invitrogen).

Bacterial strains NR17041 and NR12404 were provided by Roel M. Schaaper (Gawel et al., *Journal of Bacteriology* 190(21), 6931-9 (2008)). Both contain the lacZ(CC104) allele from Cupples and Miller's strain CC104 which reverts to a Lac$^+$ phenotype by a G·C→T·A transversion mutation that has been shown sensitive to dinB induced mutation (Cupples et al., *Proc Natl Acad Sci USA* 86(14), 5345-9 (1989); Kim et al., *Proc Natl Acad Sci USA* 94(25), 13792-7 (1997)). NR17041 contains this allele on an F' episome, while in NR12404, this allele has been placed on the chromosome (Gawel et al., *Journal of Bacteriology* 190(21), 6931-9 (2008)). Additionally, in NR17041, dinB has been replaced with kanamycin resistance markers on both the episome and chromosome (Gawel et al., *Journal of Bacteriology* 190(21), 6931-9 (2008)).

In order to compare mutation on an F' episome and on the chromosome, NR12404 and NR17041 were modified to be more genetically similar. A lambda red recombinase method was used to replace the chromosomal dinB copy with a chloramphenicol resistance maker. This method was also used to remove the entire lacIZYA operon from the F' episome of strain NR17041. This method has been described elsewhere and is effective for inactivation of genes on the chromosome and on episomes (Datsenko et al., *Proc Natl Acad Sci USA* 97(12), 6640-5 (2000); Smailus et al., *Syst Synth Biology* 1(3), 139-44 (2007)). Plasmids pKD46, pKD3, and pCP20 were obtained from the Coli Genetic Stock Center at Yale University. Briefly, NR12404 and NR17041 were transformed with plasmid pKD46 carrying the lambda red recombinase gene. These cells were grown in the presence of arabinose to induce expression of the recombinase, made electrocompetent, and were then transformed by electroporation with polymerase chain reaction (PCR) products made from template plasmid pKD3 using primers 9 and 10 for dinB knockout and primers 11 and 12 for lacIZYA knockout. Recombinant colonies were selected for on LB plates with 25 μg/ml chloramphenicol (cm25). Insertion of the chloramphenicol resistance gene was verified by PCR with flanking primers 13 and 14 for dinB and 15 and 16 for LacIZYA from template genomic DNA isolates. Genomic DNA was isolated using a Nucleospin® Tissue kit (Machery-Nagel). PCR products were compared with those from template genomic DNA isolates of the original strains. In addition to screening for insertion of the chloramphenicol resistance marker, removal of dinB and lacIZYA was verified by PCR using primers internal to dinB and lacZ, 1 and 2 and 17 and 18 respectively. Plasmid pKD46 was removed from these strains by growth at 43° C. followed by isolation of single colonies and screening for chloramphenicol resistance and ampicillin susceptibility. The resulting strains were MR1 and MR2. Strain MR1 has the genotype of NR12404 ΔdinB1::cm and strain MR2 has the genotype of NR17041F'(ΔlacIZYA::cm).

While screening confirmed that lacIZYA had been successfully replaced by the chloramphenicol resistance marker in the case of the episome of Strain MR2, PCR with primers internal to dinB for strain MR1 revealed that dinB had not been completely removed from this strain. Based on the method of construction of NR12404, it was hypothesized that in addition to the chromosomal copy of dinB, an episomal dinB copy from strain CC104 had been transferred to the chromosome along with the lacZ(CC104) allele (Gawel et al., *Journal of Bacteriology* 190(21), 6931-9 (2008)). This second dinB copy was knocked out by inserting another chloramphenicol resistance marker within this dinB gene and in the reverse orientation.

The chloramphenicol resistance marker from the first dinB knockout attempt was excised using pCP20 as previously described (Datsenko et al., *Proc Natl Acad Sci USA* 97(12), 6640-5 (2000); Cherepanov et al., *Gene* 158(1), 9-14 (1995)). Plasmid pCP20 was then cured by growth at 43° C. followed by isolation of single colonies, and screening for ampicillin and chloramphenicol sensitivity yielding strain MR3 with the genotype of NR12404 ΔdinB1. Then this strain was retransformed with pKD46 and the knockout protocol for dinB was repeated with linear PCR products prepared from pKD3 using primers 19 and 20. After this second knockout and selection on LB cm25 plates, pKD46 was cured by growth at 43° C., single colonies isolated, and screening for chloramphenicol resistance and ampicillin sensitivity was performed. Isolated genomic DNA from this strain, called MR4 with the genotype of NR12404 ΔdinB1 ΔdinB2::cm, was PCR screened as before for insertion of the chloramphenicol resistance marker using primers 1 and 2, flanking the insertion site, and for dinB deletion using primers 21 and 22, internal to dinB. This time, screening verified complete removal of dinB.

To further explore the hypothesis that NR12404 originally contained two dinB copies, end-point quantative PCR (qPCR) was performed using 50 ng of RNAase A treated genomic DNA isolates from NR12404, MR3, and MR4. This DNA was brought to 8 µl with MilliQ water, 10 µl of Taq 2× Master Mix was added (New England Biolabs), 1 µl each of primers 21 and 22 were added per tube, and PCR was performed with 15 amplification steps. Duplicate tubes with primers 23 and 24, amplifying a portion of 16s ribosomal RNA (rRNA) were also included. Products were run on TAE agarose gel, stained with ethidium bromide, and images taken. This protocol was repeated three times and ImageJ® was used to compare the integrated densities of dinB bands normalized to the integrated densities of 16s rRNA bands from the same strain and amount of DNA. This confirmed more dinB template in genomic DNA isolated from NR12404 than in genomic DNA isolated from MR3 and no template in MR4.

MR4 was transformed separately with pPro30 (empty vector) and pPro30-dinB yielding strains MR5 and MR6, respectively. Then each of these strains was conjugated with NR17041 F'(ΔLacIZYA::cm), and positive colonies were selected by growth on selective LB amp100, 50 µg/ml kanamycin (kan50), cm25 plates. This yielded the two chromosomal mutation test strains, MR7 and MR8, carrying pPro30 and pPro30-dinB respectively.

Conjugations were carried out by first growing cultures of strains to be used to an OD600 of approximately 1.0 without antibiotics, then adding 1 ml of each culture to 2 ml of fresh LB in sterile tubes. These tubes were incubated 30 minutes at 37° C. to allow conjugation to occur without shaking, then shaken at 250 rpm for 2 minutes in an attempt to break up mating pairs. Finally 1, $10^{-2}$, $10^{-4}$, and $10^{-6}$ fold serial dilutions were prepared from the conjugation mixture. 100 µl of each of these serial dilutions, as well as the original mixture, was plated on LB plates with appropriate antibiotics to select for the desired conjugant.

Strain NR17041 was transformed separately with pPro30 and pPro30-dinB, yielding strains MR9 and MR10 respectively. The resulting strains, ready for mutation testing, are all complete dinB deletion mutants on both the episome and chromosome, all carry an F' episome with the lacZ(CC104) allele, and carry either pPro30 or pPro30-dinB for propionate inducible overexpression of potential mutator gene dinB.

Verification of Propionate Induced Control Over dinB and recA730 Expression

RT-qPCR was used to verify controlled propionate-induced expression of dinB. Strains MR8 and MR10 were grown in 2 ml LB medium with appropriate antibiotics in tubes labeled for later addition of 0 mM, 0.50 mM, 5.0 mM, or 50 mM of sodium propionate. Strains MR7 and MR9 were also grown in 2 ml LB medium with appropriate antibiotics in tubes labeled for later addition of 0 mM and 50 mM sodium propionate. In total, 12 tubes were grown at 37° C., 250 rpm to an optical density at 600 nm (D0600) of ~0.5 (growth took approximately 5 hours). At this time, sodium propionate inducer was added at the labeled concentrations and growth continued for 2 more hours.

0.5 ml was harvested from each of the 12 cultures and RNA was isolated using a RiboPure™-Bacteria kit (Applied Biosystems). A DNase I treatment was also performed on isolated RNA as described in the kit instructions to remove any residual DNA. Reverse transcription was performed on 100 ng of purified RNA using a SuperScript® First-Strand Synthesis System for RT-PCR (Invitrogen). Once cDNA for each strain and induction condition was recovered, end-point qPCR was used to compare transcript levels for dinB. qPCR was performed using 10 µl of Taq 2× Master Mix (New England Biolabs), 2 µl cDNA, and 1 µl each of primers 21 and 22 for dinB detection. Duplicate qPCR tubes were prepared using primers 23 and 24, amplifying a segment of 16s rRNA. 24 amplification cycles were carried out and qPCR products were run on TAE agarose gel, stained with ethidium bromide, and images taken. The integrated density for each amplified qPCR band was measured in ImageJ® and normalized to that of the respective 16s rRNA band. qPCR confirmed that dinB transcript increased with propionate induction and no dinB transcript was detected in control strains lacking dinB expression.

Generation of Growth Curves

Strains MR7, MR8, MR9, and MR10 were first streaked on M9 glu amp100, kan50, (cm25—when appropriate) plates and grown at 37° C. to isolate single colonies. One colony per strain was inoculated into 2 ml M9 glucose medium and grown for 16 hours at 37° C., 250 rpm, then removed and the OD600 was measured for each cultured strain. 8 culture tubes were prepared with 6 ml LB medium, tubes 1-4 containing amp100, kan25 and tubes 5-8 containing amp100, kan25, cm25. Groups of tubes 1-4 and 5-8 each received 0 mM, 0.50 mM, 5.0 mM, and 50 mM sodium propionate respectively. 16 1.5 ml sterile tubes were labeled for each strain and propionate condition. 1 ml of LB with appropriate antibiotics and inducer was added to each of these from the prepared culture tubes 1-8. Strains were inoculated into the 1.5 ml tubes at an OD600 of 0.01. 3×250 µl of each strain and condition was pipette into three wells on a 96 well microplate (48 wells total). In addition 3 culture tubes were prepared with 3 ml LB, amp100, kan25, and 0 mM sodium propionate and these were also inoculated with strain MR9 at an OD600 of 0.01. Initial OD600 readings were taken from these three tubes and the entire microplate and then all were incubated at 37° C., 200 rpm. The microplate was covered and placed into a box with moist paper towels to minimize evaporation during incubation. OD600 measurements of the microplate and tubes were taken every 30 minutes for 7 hours.

The average OD600 readings for the three culture tubes were plotted over the average readings for the corresponding microplate wells. A linear relationship was observed and a regression resulted in an equation to calibrate microplate readings to OD600 readings with a 1 cm path length blanked to plain LB culture medium. Corrected average OD600 readings from each group of three microplate wells, corresponding with a particular strain and condition, were plotted over time. Growth curves indicated comparable growth characteristics for all strains and conditions except that growth at 50 mM sodium propionate was observed to be slightly slower regardless of strain.

Fluctuation Tests

Day 1: Strains were streaked from glycerol freezer stocks onto M9 glu plates containing appropriate antibiotics and grown for 24-36 hours until colonies formed. In a single test, either chromosomal or episomal mutation was evaluated. Three plates were streaked per test with either MR7 and MR8 or MR9 and MR10.

Day 2: 8 tubes, labeled 1 through 8 were prepared in two groups of 4. Each group of 4 contained sodium propionate in 0, 0.50, 5.0, and 50 mM concentrations (1-4, 5-8 respectively). Each tube also contained 2 ml LB medium and appropriate antibiotics for the strain to be inoculated. A single colony was picked up from a Day 1 M9 glu plate, carefully resuspended by gentle swirling in 25 µl LB in a sterile 1.5 ml tube, and 4 µl was inoculated into each of five tubes. Tubes 1-4 were inoculated with strains carrying pPro30, and 5-8 with strains carrying pPro30-dinB. These tubes were grown for 12 hours at 37° C. with shaking at 250 rpm.

Day 3: Culture tubes were removed from the incubator and 1 ml was transferred to each of 8 sterile 1.5 ml tubes, each corresponding to one of the 8 culture tubes. These tubes were centrifuged for 5 minutes at 3000 g to pellet cells and the medium was poured off. The cells were then resuspended in 1 ml 66 mM pH 7.2 phosphate buffer by gentle pipetting. The cells were centrifuged for another 5 minutes at 3000 g, the phosphate buffer poured off, and resuspended in another 1 ml phosphate buffer. The cells were then centrifuged a final time for 5 minutes at 3000 g, the phosphate buffer poured off and resuspended in yet another 1 ml phosphate buffer. Serial dilutions were prepared in using 66 mM pH 7.2 phosphate buffer as a dilutant from the original washed cells (1×) to $10^{-2}$, $10^{-4}$, $10^{-6}$, and $10^{-7}$ fold. For chromosomal mutation test strains, MR7 and MR8, 200 µl of the $10^{-7}$× dilutions were plated on M9 glu plates for estimation of viable cells and 200 µl of 1× was plated on M9 lac plates for determination of $Lac^+$ revertants. For episomal mutation test strains, MR9 and MR10, 200 µl of the $10^{-7}$× dilutions were plated on M9 glu plates for estimation of viable cells and 200 µl of 1× was plated on M9 lac plates for determination of $Lac^+$ revertants except in the case of strains carrying pPro30-dinB when 200 µl of the $10^{-2}$× dilutions were plated on M9 lac plates for determination of $Lac^+$ revertants. Dried plates were incubated inverted at 37° C. and their time of incubation recorded.

Day 5: The number of colonies on each plate was counted and recorded after 48 hours of incubation at 37° C.

Calculating Mutants per Culture and Mutation Rates

The number of $Lac^+$ colonies counted on M9 lac plates was used to determine the number of mutants per culture (m). When the proportion of cultures without mutants ($p_0$) was in the range $0.7 \geq p_0 \geq 0.1$ ($0.3 \leq m \leq 2.3$), the $p_0$ Method was used to calculate m with a correction applied to account for the fact that a fraction of initial culture was plated (Foster, *Methods Enzymol* 409, 195-213 (2006); Luria et al., *Genetics* 28(6), 491-511 (1943); Jones, *Mutat Res* 292(2), 187-9 (1993); Stewart, *Genetics* 137(4), 1139-46 (1994)). When the median observed mutants ($\tilde{r}$) was in the range $3 \leq \tilde{r} \leq 40$ ($1.5 \leq m \leq 10$), Jones Median Estimator was used to calculate m, this calculation was also corrected for the fraction of culture plated (Foster, *Methods Enzymol* 409, 195-213 (2006); Jones et al., *Genetics* 136(3), 1209-16 (1994)). In cases when either method could be used, the Jones Median Estimator was preferred because the $p_0$ method is inefficient in its use of data (Foster, *Methods Enzymol* 409, 195-213 (2006)). The mutation rate (µ) was determined by multiplying m by $\ln(2)/N_t$, or the natural logarithm of 2 over the final number of cells in the culture, as described by Foster, 2006 for asynchronously growing cells (Foster, *Methods Enzymol* 409, 195-213 (2006)). The final number of cells in culture was approximated from colony counts of M9 glu plates. The plating efficiency was assumed equal to 1. Distributions of the number of colonies counted on M9 glu plates were checked for normality using the Anderson-Darling test in MINITAB. In three of the fluctuation tests for each strain, the same amounts of the $10^{-7}$× dilutions plated on M9 glu plates were plated on LB plates to test the assumed plating efficiency of 1 on M9 plates.

Fluctuation tests were carried out per strain and set of conditions and median values for m were determined. Confidence limits were determined for these median mutants per culture values by using a table to calculate the binomial probability for each possible rank value for the given population size n=number of fluctuation tests, and p=0.5. Experimental sample values were ordered and assigned to these rank values. The confidence limits for the median are the actual sample values corresponding to the rank values which symmetrically include 95% probability (Foster, *Methods Enzymol* 409, 195-213 (2006)). These confidence limits were multiplied by $\ln(2)/N_t$ to approximate 95% confidence limits around the median mutation rates (Foster, *Methods Enzymol* 409, 195-213 (2006)).

Example 2

This Example describes the general materials and methods utilized in certain exemplary experiments. The results of these experiments showed that specific and targeted mutagenesis of a target gene could be achieved in *E. coli* by expressing both DNA Polymerase IV and the GeneII nickase using a propionate inducible promoter from an integrated chromosomal location, and by placing the target gene on a plasmid vector and flanked by nickase recognition sequences.

Bacterial Strains and Plasmids

Strains ER1793 and ER1821 and plasmid pBR322 were obtained from New England Biolabs. Strain EC100D pir-116 was obtained from Epicentre Biotechnologies. pPro18, pBMT-1, and pBMT-2 (Addgene plasmids 17806, 22840, and 22839) were purchased (Lee et al., *Applied Environ Microbiology* 71(11), 6856-62 (2005); Lynch et al., *Biotechnol Bioeng* 94(1), 151-8 (2006)). pCRS4 was provided by Patricia Foster (Rodriguez et al., *Journal of Bacteriology* 184(20), 5599-608 (2002)). Strain NR17041 was provided by Roel Schaaper (Gawel et al., *Journal of Bacteriology* 190(21): 6931-9 (2008)). pUC18R6K-mini-Tn7T-gm and pTNS2 were provided by Herbert Schweizer (Choi et al., *Nat Protoc* 1(1), 153-61 (2006)). pKD46 and pKD3 were obtained from the Coli Genetic Stock Center (Datsenko et al., *Proc Natl Acad Sci USA* 97(12), 6640-5 (2000)). Plasmids pLA230 and pLA2800 as well as strains JS200WT and JS200EP1 containing plasmids pHSG576-WT and pHSG576-EP respectively for expression of wild type and error prone DNA polymerase I were provided by Manel Camps (Camps et al., *Proc Natl Acad Sci USA* 100(17), 9727-32 (2003)). Plasmid pIDTS-MART-CNMNC was ordered from Integrated DNA Technologies and was designed to contain a multiple cloning site flanked by two target sites for the GeneII nickase (5'-GTTGT-TCCAGTTTGGAACAAGAGTCCACTATTAAAGA-3', SEQ ID NO:50) and flanked by 5 repeated Chi sequences (5'-GCTGGTGG-3', SEQ ID NO: 51) on either side (Rodriguez et al., *Journal of Bacteriology* 184(20), 5599-608 (2002)).

Molecular Cloning and Strain Manipulation.

PCR amplifications were performed with a Phusion High-Fidelity PCR Kit (New England Biolabs) except for colony PCR used to screen for correct cloning, which were performed using Taq 2× Master Mix (New England Biolabs). PCR reactions were carried out according to the manufacturer's recommendations and, when used to produce cloning inserts, were gel purified using NucleoSpin Extract II Kit (Clontech). Restriction enzymes were purchased from New England Biolabs and digests were performed according to the manufacturer's recommendations. Cloning of inserts into vectors was performed by gel purifying digested vector and insert DNA using a NucleoSpin Extract II Kit (Clontech) and ligating the insert into the vector using T4 DNA Ligase (New England Biolabs). Competent cells were prepared using either the method described by Chung et al. (1989) (Chung et al., *Proc Natl Acad Sci USA* 86(7), 2172-5 (1989) or, when higher transformation efficiencies were required, were made electrocompetent (Sambrook et al., *Molecular cloning: a laboratory manual* Cold Spring Harbor Laboratory Press (2001)).

Make Rapidaptor Strains

Strain ER1793 (New England Biolabs) was chosen as a parent for making Rapidaptor strains because of its utility as a cloning strain. First, the native copy of dinB in this strain was removed using the method of Datsenko and Wanner (2000). Plasmids pKD46 and pKD3 along with primers 9, 10, 13 and 14 were used for this manipulation following methods previously described (Datsenko and Wanner 2000). After a successful ΔdinB::cm deletion mutant of ER1793 had been created, this strain was cured of plasmid pKD46 by growth at 42° C. without ampicillin, followed by colony purification and screening individual colonies for amp$^S$ and cm$^R$ and named MR11. Antibiotic concentrations of 25 µg/ml chloramphenicol (cm25) and 100 µg/ml ampicillin (amp 100) were used.

Since pPro18 was constructed using the backbone of the vector pBAD18, which contains a sequence nearly identical to the recognition site of the GeneII nickase, the propionate regulated region of pPro 18 was cloned into the backbone of plasmid pBR322 (New England Biolabs) (Lee et al., *Applied Environ Microbiology* 71(11), 6856-62 (2005)). This was accomplished by amplifying the desired region from pPro18 using primers 25 and 26, and cloning of this insert between the AseI and AatII sites of pBR322, creating plasmid pProBR. This procedure also removed part of the gene providing ampicillin resistance on pBR322, so strains harboring this vector were grown on 10 µg/ml tetracycline (tc10) and screened for amp$^S$.

geneII was amplified from plasmid pCRS4 using primers 27 and 28, then gel purified and amplified again using primers 29 and 30, adding sites for restriction enzymes XmaI and XbaI, a ribosomal binding site (RBS) and 5' untranslated region (5'UTR). Amplified DNA was cloned between the XmaI and XbaI sites in pProBR creating plasmid pProBR-geneII.

dinB was amplified with primers 1 and 2 from chromosomal DNA isolated from strain ER1821 (New England Biolabs) using a NucleoSpin Tissue kit (Clontech). A further round of amplification with primers 3 and 31 added restriction sites for SacI and XmaI a RBS and a 5'UTR. This insert was cloned between the SacI and XmaI sites of pProBR-geneII forming pProBR-dinB-geneII.

Primers 32 and 33 were used to amplify a region pProBR-dinB-geneII, adding restriction sites for ApaI and SpeI. This insert was cloned into pUC18R6K-mini-Tn7T-gm digested with these enzymes. The resulting vector was pUC18R6K-mini-Tn7T-gm-Ppro-dinB-geneII. An additional plasmid was constructed for performing mini-Tn7 insertions by digesting pUC18R6K-mini-Tn7T-gm-Ppro-dinB-geneII with StuI and using an In-Fusion PCR Cloning Kit (Clontech) to insert a lacZ(CC104) allele under control of its native promoter, which had been amplified chromosomal DNA isolated from strain NR17041 using a NucleoSpin Tissue Kit (Clontech). Primers 34 and 35 were used to amplify lacZ (CC104) and to add sequence homology required for the In-Fusion PCR Cloning Kit (Clontech). The resulting plasmid was pUC18R6K-mini-Tn7T-gm-Ppro-dinB-geneII-lacZ (CC104).

Plasmids pUC18R6K-mini-Tn7T-gm-Ppro-dinB-geneII, and pUC18R6K-mini-Tn7T-gm-Ppro-dinB-geneII-lacZ (CC104) were used along with pTNS2 to perform mini-Tn7 insertions into ER1793ΔdinB::cm as previously described (Choi et al., *Nat Protoc* 1(1), 153-61 (2006)). The resulting strains were named MR12 and MR13. Screening for correct insertions was performed using primers 36, 37, 38, and 39.

Make pRapt Plasmids

The first generation of mutation target plasmids were constructed by first annealing approximately 1 µg each of primers 40 and 41. This was performed by heating a mixture of these primers in a total volume of 20 µl milliQ H$_2$O to 95° C. for 5 minutes, followed by slow cooling to 25° C. The annealed primers were then digested with XbaI and HindIII and cloned into plasmid pBMT-1 digested with the same enzymes resulting in pBMT1-MCS. Next, primers 42 and 43 were annealed, digested, and cloned between the XbaI and SacI restriction sites in pBMT1-MCS creating pBMT1-MCS-NickR. pBMT-MCS-NickR and pBMT1-MCS were digested with BsrBI, and after gel purification, ligated, removing the mob gene from these vectors and creating pBT1-MCS-NickR and pBT1-MCS. Next, the lacZ(CC104) allele was amplified from NR17041 genomic DNA using primers 44 and 45 and cloned between the PstI and XhoI sites in vectors pBT1-MCS, pBT1-MCS-NickR, and pBMT1-MCS-NickR creating pBT1-MCS-lacZ(CC104), pBT1-MCS-NickR-lacZ (CC104), and pBMT1-MCS-NickR-lacZ(CC104). Finally primers 46 and 47 were annealed, digested and cloned between the HindIII and KasI sites in pBMT1-MCS-NickR and pBMT1-MCS-NickR-lacZ(CC104) creating pBT1-MCS-2XNickR and pBT1-MCS-2XNickR-lacZ(CC104).

The second generation of mutation target plasmids, used in bla reversion fluctuation tests, were created by cloning the XbaI-KasI segment of pIDTSMART-CNMNC into pBMT1 and pBMT2 digested with these two enzymes creating plasmids pRapt2-Amp and pRapt2-Kan. Then, the bla allele from plasmid pLA2800 was amplified using primers 48 and 49 and cloned between the SalI and PstI sites in pRapt2-Kan creating pRapt2-Kan-bla.

Prepare Strains for Fluctuation Tests

Strain MR12 was transformed separately with plasmids pBT1-MCS-lacZ(CC104), pBT1-MCS-NickR-lacZ (CC104), pBT1-MCS-2XNickR-lacZ(CC104), and pRapt2-Kan-bla. Strain MR12 was also mated with strain NR17041 and conjugants were selected on 30 µg/ml gentamycin (gm30), cm25, kan25, 10 µg/ml streptomycin (str10) LB plates. Strain MR13 was transformed with plasmid pBT1-MCS-2XNickR. Strains JS200WT and JS200EP1 were separately transformed with vectors pLA230 and pLA2800 in order to reproduce strains used by Camps et al. (*Proc Natl Acad Sci USA* 100(17), 9727-9732 (2003)) in their experiments.

List of Strains, Plasmids and Primers Described in Examples 1-2

| | Description | Source |
|---|---|---|
| Bacterial Strains | | |
| NR12404 | MG1655 with lacZ(CC104) on its chromosome and two chromosomal dinB copies | (Gawel et al. 2008) |

-continued

| Description | Source |
|---|---|
| NR17041 | ara thi Δ(prolac) trpE9777 ΔdinB::kan FCC104/ΔdinB::kan | (Gawel et al. 2008) |
| ER1793 | F⁻ fhuA2 Δ(lacZ)r1 glnV44 e14⁻(McrA⁻) trp-31 his-1 rpsL104 xyl-7 mtl-2 metB1 Δ(mcrC-mrr)114::IS10 | New England Biolabs |
| ER1821 | F⁻ glnV44 e14⁻(McrA⁻) rfbD1? relA1? endA1 spoT1? thi-1 Δ(mcrC-mrr)114::IS10 | New England Biolabs |
| EC100D pir-116 | F⁻ mcrA Δ(mrr-hsdRMS-mcrBC) φ80dlacZΔM15 ΔlacX74 recA1 endA1 araD139 Δ(ara, leu)7697 galU galK λ-rpsL (Str^R) nupG pir-116(DHFR) | Epicentre Biotechnologies |
| JS200WT | SC-18 recA718 polA12 uvrA155 trpE65 lon-11 sulA1 | (Camps et al. 2003) |
| JS200EP1 | SC-18 recA718 polA12 uvrA155 trpE65 lon-11 sulA1 | (Camps et al. 2003) |
| MR1 | NR12404 ΔdinB1::cm | Example 1 |
| MR2 | NR17041 FNR17041/ΔlacIZYA::cm | Example 1 |
| MR3 | NR12404 ΔdinB1 | Example 1 |
| MR4 | NR12404 ΔdinB1 ΔdinB2::cm | Example 1 |
| MR5 | MR4 carrying pPro30 | Example 1 |
| MR6 | MR4 carrying pPro30-dinB | Example 1 |
| MR7 | MR5 FMR2 | Example 1 |
| MR8 | MR6 FMR2 | Example 1 |
| MR9 | NR17041 carrying pPro30 | Example 1 |
| MR10 | NR17041 carrying pPro30-dinB | Example 1 |
| MR11 | ER1793 ΔdinB::cm | Example 2 |
| MR12 | MR1 mini-Tn7T-gm-Ppro-dinB-geneII | Example 2 |
| MR13 | MR1 mini-Tn7T-gm-Ppro-dinB-geneII-lacZ(CC104) | Example 2 |
| Plasmids | | |
| pPro30 | Propionate inducible expression vector | (Lee and Keasling 2005) |
| pPro30-dinB | Propionate inducible expression vector carrying dinB gene for inducible expression | Example 1 |
| pBR322 | | New England Biolabs |
| pPro18 | | (Lee and Keasling 2005) |
| pBMT-1 | | (Lynch and Gill 2006) |
| pBMT-2 | | (Lynch and Gill 2006) |
| pCRS4 | | (Rodriguez et al. 2002) |
| pUC18R6K-mini-Tn7T-gm | | (Choi and Schweizer 2006) |
| pTNS2 | (Choi and Schweizer 2006) |
| pKD46 | (Datsenko and Wanner 2000) |
| pKD3 | (Datsenko and Wanner 2000) |
| pCP20 | (Datsenko and Wanner 2000) |
| pLA230 | (Camps et al. 2003) |
| pLA2800 | (Camps et al. 2003) |
| pIDTSMART-CNMNC | Example 2 |
| pProBR | Example 2 |
| pProBR-geneII | Example 2 |
| pProBR-dinB-geneII | Example 2 |
| pUC18R6K-mini-Tn7T-gm-Ppro-dinB-geneII | Example 2 |
| pUC18R6K-mini-Tn7T-gm-Ppro-dinB-geneII-lacZ(CC104) | Example 2 |
| pBMT1-MCS | Example 2 |
| pBMT1-MCS-NickR | Example 2 |
| pBT1-MCS | Example 2 |
| pBT1-MCS-NickR | Example 2 |
| pBT1-MCS-lacZ(CC104) | Example 2 |
| pBT1-MCS-NickR-lacZ(CC104) | Example 2 |
| pBMT1-MCS-NickR-lacZ(CC104) | Example 2 |
| pBT1-MCS-2XNickR | Example 2 |
| pBT1-MCS-2XNickR-lacZ(CC104) | Example 2 |
| pRapt2-Amp | Example 2 |
| pRapt2-Kan | Example 2 |
| pRapt2-Kan-bla | Example 2 |

| Primers (SEQ ID NO) | Sequence |
|---|---|
| 1 | 5'-ATGCGTAAAATCATTCATGTGGATA-3' |
| 2 | 5'-TCATAATCCCAGCACCAGTTGTCTT-3' |
| 3 | 5'-AAAGAGCTCAGGAGGCAGCTAATGCGTAAAATCATT-3' |
| 4 | 5'-GCGTCTAGATCATAATCCCAGCACCAG-3' |
| 5 | 5'-GGCACACCCCTTGCT-3' |
| 6 | 5'-CCGCTTCTGCGTTCT-3' |
| 7 | 5'-CGCCTCCGACATGAA-3' |
| 8 | 5'-CTTTGCCGACGCCGG-3' |
| 9 | 5'-ATGCTGAATCTTTACGCATTTCTCAAACCCTGAAATCACTGTATACTTTAGTGTAGGCTGGAGCTGCTTC-3' |
| 10 | 5'-CAGTGATACCCTCATAATAATGCACACCAGAATATACATAATAGTATACAATGGGAATTAGCCATGGTCC-3' |

-continued

| Primers (SEQ ID NO) | Sequence |
|---|---|
| 11 | 5'-GTGAAACCAGTAACGTTATACGATGTCGCAGAGTATGCCGGTGTCTCTTAGTGTAGGCTGGAGCTGCTTC-3' |
| 12 | 5'-TTAAACTGACGATTCAACTTTATAATCTTTGAAATAATAGTGCTTATCCCATGGGAATTAGCCATGGTCC-3' |
| 13 | 5'-ATGCTGAATCTTTACGCATTTCTCA-3' |
| 14 | 5'-CAGTGATACCCTCATAATAATGCAC-3' |
| 15 | 5'-GTGAAACCAGTAACGTTATACGATG-3' |
| 16 | 5'-CTGACGATTCAACTTTATAATCTTTGAAAT-3' |
| 17 | 5'-GCGCAACGCAATTAATGTGAGTTAGCTCAC-3' |
| 18 | 5'-TTATTTTTGACACCAGACCAACTGGTAATGGTAGC-3' |
| 19 | 5'-ATGCGTAAAATCATTCATGTGGATATGGACTGCTTTTTCGCCGCAGTGGAGTGTAGGCTGGAGCTGCTTC-3' |
| 20 | 5'-TCATAATCCCAGCACCAGTTGTCTTTCCATTTGCGGGTCAAGCAACGTCAATGGGAATTAGCCATGGTCC-3' |
| 21 | 5'-CTGGATGAGGCTTATCTCGATGTC-3' |
| 22 | 5'-GACCAGTGATGAATATCTTCCGCC-3' |
| 23 | 5'-CAGCCACACTGGAACTGAGA-3' |
| 24 | 5'-GTTAGCCGGTGCTTCTTCTG-3' |
| 25 | 5'-AAAATTAATTCAGCTTTTCAGCCGCCGCC-3' |
| 26 | 5'-GGGGACGTCTGTATTTAGAAAAATAAACAAAAGAGTTTG-3' |
| 27 | 5'-ATGATTGACATGCTAGTTTT-3' |
| 28 | 5'-TTATGCGATTTTAAGAACTG-3' |
| 29 | 5'-AAACCCGGGAGGAGGCAGCTAATGATTGACATGCTAGTTTT-3' |
| 30 | 5'-GGGTCTAGATTATGCGATTTTAAGAACTGGCTC-3' |
| 31 | 5'-AAACCCGGGTCATAATCCCAGCACCAG-3' |
| 32 | 5'-TTTACTAGTTCAGCTTTTCAGCCGCCGCCAGAAC-3' |
| 33 | 5'-AAAGGGCCCGCAAAAAGGCCATCCGTCAGGATG-3' |
| 34 | 5'-GGTACCTCGCGAAGGGCGCAACGCAATTAATGTGAG-3' |
| 35 | 5'-GGTTGGCCTGCAAGGTTATTTTTGACACCAGACCAACTGG-3' |
| 36 | 5'-AAGTAGCGATAACATGCACATCATC-3' |
| 37 | 5'-CACAGCATAACTGGACTGATTTC-3' |
| 38 | 5'-ATTAGCTTACGACGCTACACCC-3' |
| 39 | 5'-AAGAACCGATACCCTGGTAGTTAA-3' |
| 40 | 5'-AAATCTAGAGGTACCGAGCTCCTGCAGACTCGTCTCGAGCCCGGGAAGCTTAAA-3' |
| 41 | 5'-TTTAAGCTTCCCGGGCTCGAGACTAGTCTGCAGGAGCTCGGTACCTCTAGATTT-3' |
| 42 | 5'-AAAGAGCTCGTCTTTAATAGTGGACTCTTGTTCCAAACTGGAACAACGTCTAGAAAA-3' |
| 43 | 5'-TTTTCTAGACGTTGTTCCAGTTTGGAACAAGAGTCCACTATTAAAGACGAGCTCTTT-3' |
| 44 | 5'-AAACTGCAGGCGCAACGCAATTAATGTGAG-3' |
| 45 | 5'-AAACTCGAGTTATTTTTGACACCAGACCAACTGG-3' |
| 46 | 5'-AAAGGCGCCGTCTTTAATAGTGGACTCTTGTTCCAAACTGGAACAACGAAGCTTAAA-3' |

-continued

| Primers (SEQ ID NO) | Sequence |
|---|---|
| 47 | 5'-TTTAAGCTTCGTTGTTCCAGTTTGGAACAAGAGTCCACTATTAAAGACGGCGCCTTT-3' |
| 48 | 5'-AAAGTCGACGCACCCGACATAGATCCCCTATTTG-3' |
| 49 | 5'-AAACTGCAGAAACTTGGTCTGACAGTTACCAATGCTTAATC-3' |

Example 3

A Condition-Driven Rapidly Adaptable Bacterial Strain that can be Stimulated to Mutate by an External Stressor Stress promoters are well-characterized for *E. coli* and include several sigma factors as well as central metabolic, anabolic and motility genes. Further, the quorum sensing system (autoinducer 2) provides a host of promoters sensitive to external stimuli. For *Pseudomonas*, there are genes associated with the degradation of various contaminants and with the resistance of various antimicrobials that have been sequenced and whose transcriptional regulation is understood. For example, the sep controller region from *P. putida* is activated under several different organic pollutants and has been utilized in the development of a biosensor for benzene, toluene, ethylbenzene, and all three isomers of xylene (BTEX), naphthalene, and complex mixtures of aliphatic and aromatic hydrocarbons (Phoenix et al., *Environmental Microbiol* 5(12): 1309-27 (2003)). The sep promoter region from *P. putida* has been combined with the luxCDABE operon from *Photorhabdus luminescens* for the detection of available contaminants in soil. Similarly, the multidrug efflux pump system of *P. aeruginosa* is activated through ligand binding to the MexZ operon (Morita et al., *J. Bacteriol* 188(5): 1847-55 (2006)), and the tod operon of *P. putida* is activated by BTEX and trichloroethylene (Applegate et al., *Appl Environ Microbiol* 64(7): 2730-5 (1998); Shingleton et al., *Appl Environ Microbiol* 64(12): 5049-52 (1998)). In all cases, a broad range of potential degradation targets activate expression of a single operon or gene. Broad-ranged regulatory elements could be used to drive expression of mutational genes, including Pol IV and Pol V.

*P. aeruginosa* cell lines expressing Pol IV under control of sep. To test the ability of extracellular stimuli to induce adaptation at a rate consistent with contaminant concentration, the sep promoter region from *P. putida* is used to drive expression of Pol IV. Using a similar experimental design as described earlier, the ability of engineered strains to be induced by external stimuli to undergo mutation for various times under various stressors (contaminants) is investigated. Specifically, *Pseudomonas* sp harboring gene constructs that tie expression of Pol IV and/or Pol V to sep for contaminant-controlled mutation are tested in chemostat cultures under various loads of naphthalene. While mutation rates are determined by $Rif^R$ as they were before, the ability of cells to utilize naphthalene as a sole carbon source for proliferation are recorded. Higher degradation rates are one of the outcomes of enhanced mutation rates under naphthalene loading.

*E. coli* cell lines expressing Pol IV and/or Pol V under control of RpoS. While it has been established that RpoS aids in controlling Pol IV and Pol V, it is only under the condition of DNA damage that Pol IV and Pol V are induced by RpoS. Hence, in order to insure higher mutation rates under any stress condition, the expression of Pol IV and Pol V are directly induced by RpoS via an RpoS binding element. Strains are tested under a variety of stressors including heat shock, high salinity, ethanol and cold shock. A plasmid bearing a nucleic acid encoding a constitutive green fluorescent protein (GFP) is co-transformed with one harboring Pol IV and/or Pol V under control of RpoS. Cells are grown to high density to induce plasmid and recombinant protein stress. Cells are subsequently be plated out to determine if any colonies have greater or less GFP expression than controls (without over-expression of Pol IV and/or Pol V and/or cultured under normal conditions without stress) and if changes in fluorescence can be correlated to changes in mutational rates via $Rif^R$.

Rapidly Adapting Strains for the Biodegradation of Perfluorochemicals.

Aerobic degradation of perfluorochemicals (particularly PFOA and PFNA) has yet to be demonstrated. Hence, a rapidly-adapting strain of bacteria known for degrading harmful organics provides both clues as to which pathways would be involved in degradation as well as an organism that can at least partially degrade some of these compounds.

To determine the relative toxicity of PFOA and PFNA on *Pseudomonas* sp and *E. coli*, cultures with varying amounts of PFOA and PFNA are incubated for various times. In these experiments, PFOA serves as both sole- and secondary-carbon source. The goal of this setup is to determine if PFOA or PFNA can be either metabolized or simply tolerated.

Cultures are incubated with varying amounts of glucose and/or PFOA or PFNA. At specific times, culture conditions are assayed for culture viability, PFAO or PFNO concentration, glucose uptake rates, $CO_2$ evolution, dissolved $O_2$, and mutational rates. Further, samples are assayed by RT-PCR for transcripts from MexZ-related genes to determine if contaminant pumping mechanisms are actively upregulated in the presence of PFOA or PFNA.

Test the Ability of *Pseudomonas* sp to Adapt to and Degrade PFOA and PFNA in Continuous Culture.

An attempt is made to degrade contaminants that have yet to be successfully degraded, namely PFOA and PFNA. Strains developed according to the approach disclosed herein are used for this study. By mutating exposed strains at a rate consistent with the amount of contaminant as done earlier, resistance to and metabolism of the contaminant occurs more rapidly when it is most needed. Control of mutations is determined by contaminant load, much in the way that organisms control stress responses in relation to the level of stimulating species. Alternatively, culture mutation rates are controlled exogenously with external inducer. In this system, mutation rates can be lowered or raised depending on the relative success of the strains (as determined by cell growth) in adapting to PFOA and PFNA.

Strains which respond to contaminants in accordance with the level of contaminant in the feed stream are more robust and will "converge" at a degrading strain more rapidly. Alternatively, rates of mutation can be artificially increased or decreased while holding the level of contaminant steady at a low level.

What is claimed is:

1. A method of generating mutations within a target DNA comprising:
providing a host bacterial strain, which comprises a nucleic acid coding for an error-prone DNA polymerase under control of an inducible transcriptional regulatory region, a nucleic acid coding for a nicking enzyme, and a plasmid vector comprising said target DNA placed in proximity to at least one recognition site of said nicking enzyme, and
culturing said strain under conditions that permit the expression of said error-prone DNA polymerase and said nicking enzyme, thereby generating mutations within said target DNA.

2. The method of claim 1, wherein said error-prone DNA polymerase is a bacterial DNA polymerase IV (Pol IV) or a bacterial DNA polymerase V (Pol V).

3. The method of claim 1, wherein said nicking enzyme is Nickase encoded by gene II, and wherein the recognition site of said Nickase comprises the nucleotide sequence as set forth in SEQ ID NO: 50.

4. The method of claim 1, wherein the nucleic acid coding for the nicking enzyme is also under control of an inducible transcriptional regulatory region.

5. The method of claim 4, wherein the nucleic acid coding for the error-prone DNA polymerase and the nucleic acid coding for the nicking enzyme are under control of a single inducible transcriptional regulatory region.

6. The method of claim 5, wherein the nucleic acid coding for the error-prone DNA polymerase and the nucleic acid coding for the nicking enzyme, both of which are placed under control of a single inducible transcriptional regulatory region, are integrated into the bacterial chromosome.

7. The method of claim 1 or 5, wherein said inducible transcriptional regulatory region is inducible by propionate, and comprises a prpBCDE promoter ($P_{prpB}$) and a prpR enhancer.

8. The method of claim 1 or 5, wherein said inducible transcriptional regulatory region comprises a lac promoter inducible by IPTG.

9. The method of claim 1 or 5, wherein said inducible transcriptional regulatory region comprises a stress-induced promoter.

10. The method of claim 9, wherein the stress induced promoter is responsive to an environmental pollutant or contaminant.

11. The method of claim 1, wherein said target DNA are flanked by two recognition sites of said nicking enzyme.

12. The method of claim 11, wherein said recognition sites comprise the nucleotide sequence as set forth in SEQ ID NO: 50.

13. The method of claim 12, wherein the plasmid vector which carries the target DNA flanked by two recognition sites also comprises one or multiple repeats of the Chi sequence (SEQ ID NO: 51) placed adjacent to one or both of the recognition sites.

14. The method of claim 1, wherein the target DNA comprises a prokaryotic gene.

15. The method of claim 1, wherein the target DNA comprises a eukaryotic gene.

16. The method of claim 1, wherein the target DNA encodes an enzyme and the mutagenesis results in a mutated enzyme with altered substrate specificity or enzymatic efficiency.

17. The method of claim 1, wherein cells of said host strain are transformed with a library of target DNAs.

18. The method of claim 1, further comprising selecting a bacterial cell containing a mutated target DNA for a desirable phenotype.

19. A bacterial strain, comprising a nucleic acid coding for an error-prone DNA polymerase under control of an inducible transcriptional regulatory region, a nucleic acid coding for a nicking enzyme, and a plasmid vector comprising said target DNA placed in proximity to at least one recognition site of said nicking enzyme.

20. The strain of claim 19, wherein the nucleic acid coding for the nicking enzyme is also under control of an inducible transcriptional regulatory region.

21. The strain of claim 20, wherein the nucleic acid coding for the error-prone DNA polymerase and the nucleic acid coding for the nicking enzyme are placed under control of a single inducible transcriptional regulatory region and are integrated in the bacterial chromosome.

22. A kit for targeted mutagenesis, comprising
a bacterial host strain,
an integrative or replicative vector comprising a nucleic acid coding for an error-prone DNA polymerase under control of an inducible transcriptional regulatory region and a nucleic acid coding for a nicking enzyme under control of an inducible transcriptional regulatory region, and
a plasmid vector comprising said target DNA placed in proximity to at least one recognition site of said nicking enzyme.

* * * * *

SEQUENCE LISTING

<160> NUMBER OF SEQ ID NOS: 51

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
atgcgtaaaa tcattcatgt ggata                                25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
tcataatccc agcaccagtt gtctt                                25

<210> SEQ ID NO 3
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 3
aaagagctca ggaggcagct aatgcgtaaa atcatt                    36

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 4
gcgtctagat cataatccca gcaccag                              27

<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 5
ggcacacccc ttgct                                           15

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
ccgcttctgc gttct                                           15

<210> SEQ ID NO 7
<211> LENGTH: 15
<212> TYPE: DNA

<213> ORGANISM: Artificial Sequence
<220> FEATURE:
<223> OTHER INFORMATION: Synthetic oligonucleotide

<400> SEQUENCE: 7
cgcctccgac atgaa                                                     15

<210> SEQ ID NO 8
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 8
ctttgccgac gccgg                                                     15

<210> SEQ ID NO 9
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 9
atgctgaatc tttacgcatt tctcaaaccc tgaaatcact gtatacttta gtgtaggctg    60
gagctgcttc                                                           70

<210> SEQ ID NO 10
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 10
cagtgatacc ctcataataa tgcacaccag aatatacata atagtataca atgggaatta    60
gccatggtcc                                                           70

<210> SEQ ID NO 11
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 11
gtgaaaccag taacgttata cgatgtcgca gagtatgccg gtgtctctta gtgtaggctg    60
gagctgcttc                                                           70

<210> SEQ ID NO 12
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 12
ttaaactgac gattcaactt tataatcttt gaaataatag tgcttatccc atgggaatta    60
gccatggtcc                                                           70

<210> SEQ ID NO 13
<211> LENGTH: 25
<212> TYPE: DNA

```
<213> ORGANISM: Artificial Sequence
<220> FEATURE:
<223> OTHER INFORMATION: Synthetic oligonucleotide

<400> SEQUENCE: 13
atgctgaatc tttacgcatt tctca                                            25

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
cagtgatacc ctcataataa tgcac                                            25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
gtgaaaccag taacgttata cgatg                                            25

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 16
ctgacgattc aactttataa tctttgaaat                                       30

<210> SEQ ID NO 17
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 17
gcgcaacgca attaatgtga gttagctcac                                       30

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18 ttattttga caccagacca actggtaatg gtagc                                  35

<210> SEQ ID NO 19
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 19
atgcgtaaaa tcattcatgt ggatatggac tgcttttttcg ccgcagtgga gtgtaggctg     60
```
gagctgcttc                                                            70

<210> SEQ ID NO 20
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 20
tcataatccc agcaccagtt gtctttccat ttgcgggtca agcaacgtca atgggaatta    60
gccatggtcc                                                            70

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
ctggatgagg cttatctcga tgtc                                            24

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
gaccagtgat gaatatcttc cgcc                                            24

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
cagccacact ggaactgaga                                                 20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gttagccggt gcttcttctg                                                 20

<210> SEQ ID NO 25
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 25
aaaattaatt cagcttttca gccgccgcc                                       29

<210> SEQ ID NO 26
<211> LENGTH: 39
<212> TYPE: DNA

<213> ORGANISM: Artificial Sequence
<220> FEATURE:
<223> OTHER INFORMATION: Synthetic oligonucleotide

<400> SEQUENCE: 26
ggggacgtct gtatttagaa aaataaacaa aagagtttg                              39

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
atgattgaca tgctagtttt                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
ttatgcgatt ttaagaactg                                                   20

<210> SEQ ID NO 29
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 29
aaacccggga ggaggcagct aatgattgac atgctagttt t                           41

<210> SEQ ID NO 30
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 30
gggtctagat tatgcgattt taagaactgg ctc                                    33

<210> SEQ ID NO 31
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 31
aaacccgggt cataatccca gcaccag                                           27

<210> SEQ ID NO 32
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 32
tttactagtt cagcttttca gccgccgcca gaac                                   34

<210> SEQ ID NO 33
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 33
aaagggcccg caaaaaggcc atccgtcagg atg                                33

<210> SEQ ID NO 34
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 34
ggtacctcgc gaagggcgca acgcaattaa tgtgag                             36

<210> SEQ ID NO 35
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 35
ggttggcctg caaggttatt tttgacacca gaccaactgg                         40

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 36
aagtagcgat aacatgcaca tcatc                                         25

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37
cacagcataa ctggactgat ttc                                           23

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
attagcttac gacgctacac cc                                            22

<210> SEQ ID NO 39
<211> LENGTH: 24
<212> TYPE: DNA
<213> ORGANISM: Artificial Sequence

```
<220> FEATURE:
<223> OTHER INFORMATION: Synthetic oligonucleotide

<400> SEQUENCE: 39
aagaaccgat accctggtag ttaa                                              24

<210> SEQ ID NO 40
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 40
aaatctagag gtaccgagct cctgcagact cgtctcgagc ccgggaagct taaa             54

<210> SEQ ID NO 41
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 41
tttaagcttc ccgggctcga gactagtctg caggagctcg gtacctctag attt             54

<210> SEQ ID NO 42
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 42
aaagagctcg tctttaatag tggactcttg ttccaaactg gaacaacgtc tagaaaa          57

<210> SEQ ID NO 43
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 43
ttttctagac gttgttccag tttggaacaa gagtccacta ttaaagacga gctcttt          57

<210> SEQ ID NO 44
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 44
aaactgcagg cgcaacgcaa ttaatgtgag                                        30

<210> SEQ ID NO 45
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 45
aaactcgagt tatttttgac accagaccaa ctgg                                   34
```

```
<210> SEQ ID NO 46
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 46
aaaggcgccg tctttaatag tggactcttg ttccaaactg aacaacgaa gcttaaa        57

<210> SEQ ID NO 47
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 47
tttaagcttc gttgttccag tttggaacaa gagtccacta ttaaagacgg cgccttt        57

<210> SEQ ID NO 48
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 48
aaagtcgacg cacccgacat agatcccta tttg                                  34

<210> SEQ ID NO 49
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 49
aaactgcaga aacttggtct gacagttacc aatgcttaat c                         41

<210> SEQ ID NO 50
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 50
gttgttccag tttggaacaa gagtccacta ttaaaga                              37

<210> SEQ ID NO 51
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 51 gctggtgg                                                              8
```